US012588956B2

(12) United States Patent
Sachar et al.

(10) Patent No.: US 12,588,956 B2
(45) Date of Patent: Mar. 31, 2026

(54) TRAJECTORY TRACKING FOR MEDICAL DEVICE

(71) Applicants: BOSTON SCIENTIFIC SCIMED, INC., Maple Grove, MN (US); WORCESTER POLYTECHNIC INSTITUTE, Worcester, MA (US)

(72) Inventors: Avnish Sachar, Cambridge, MA (US); Anne Gu, Brighton, MA (US); Christopher J. Nycz, Holden, MA (US); Farid Tavakkolmoghaddam, Worcester, MA (US); Hannah R. Baez, Ann Arbor, MI (US); Aditya Ambani, Brighton, MA (US); Paris Marks Saint-Preux, Lowell, MA (US); James Weldon, Newton, MA (US)

(73) Assignees: BOSTON SCIENTIFIC SCIMED, INC., Maple Grove, MN (US); WORCESTER POLYTECHNIC INSTITUTE, Worcester, MA (US)

( * ) Notice: Subject to any disclaimer, the term of this patent is extended or adjusted under 35 U.S.C. 154(b) by 412 days.

(21) Appl. No.: 18/199,218

(22) Filed: May 18, 2023

(65) Prior Publication Data

US 2023/0372034 A1 Nov. 23, 2023

Related U.S. Application Data

(60) Provisional application No. 63/344,245, filed on May 20, 2022.

(51) Int. Cl.
| | |
|---|---|
| *A61B 1/00* | (2006.01) |
| *A61B 17/00* | (2006.01) |
| *A61B 34/30* | (2016.01) |

(52) U.S. Cl.
CPC .............. *A61B 34/30* (2016.02); *A61B 17/00* (2013.01); *A61B 2017/003* (2013.01)

(58) Field of Classification Search
CPC ............ A61B 1/00039; A61B 1/00042; A61B 1/00066; A61B 1/0052; A61B 1/0016;
(Continued)

(56) References Cited

U.S. PATENT DOCUMENTS

| | | |
|---|---|---|
| 4,461,282 A | 7/1984 | Ouchi et al. |
| 5,578,052 A | 11/1996 | Koros et al. |
| | (Continued) | |

FOREIGN PATENT DOCUMENTS

| | | |
|---|---|---|
| DE | 202010009234 U1 | 12/2011 |
| JP | H09492 A | 1/1997 |
| | (Continued) | |

OTHER PUBLICATIONS

Asge, "Minimizing Occupational Hazards in Endoscopy: Personal Protective Equipment, Radiation Safety, and Ergonomics," Gastrointestinal Endoscopy Journal, vol. 72, No. 2, 9 pages, 227-235, 2010.

(Continued)

*Primary Examiner* — Timothy J Neal
(74) *Attorney, Agent, or Firm* — Seager, Tufte & Wickhem LLP

(57) ABSTRACT

A steerable medical device includes a handle and an elongate shaft extending distally from the handle to a distal tip. A motor control assembly including a motor control housing is configured to detachably interface with the handle. The motor control assembly includes a first drive assembly and a second drive assembly disposed within the motor control housing. The motor control assembly includes an input device and a controller that is operably coupled with the first drive assembly, the second drive assembly and the input (Continued)

device. The controller is configured to control operation of the first drive assembly and/or the second drive assembly in order to move the distal tip, receive one or more user inputs from a user via the input device, and to modify operation of the first drive assembly and/or the second drive assembly in accordance with the received one or more inputs.

19 Claims, 16 Drawing Sheets

(58) Field of Classification Search
CPC ..... A61B 1/009; A61B 1/00105; A61B 17/00;
A61M 25/0133
See application file for complete search history.

(56) References Cited

U.S. PATENT DOCUMENTS

| | | | | |
|---|---|---|---|---|
| 5,658,238 | A * | 8/1997 | Suzuki | A61B 1/009 600/150 |
| 6,325,808 | B1 * | 12/2001 | Bernard | A61B 34/30 606/139 |
| 7,682,358 | B2 | 3/2010 | Gullickson et al. | |
| 7,686,816 | B2 | 3/2010 | Belef et al. | |
| 7,789,825 | B2 | 9/2010 | Nobis et al. | |
| 8,007,432 | B2 | 8/2011 | Vakharia et al. | |
| 8,808,168 | B2 | 8/2014 | Ettwein et al. | |
| 9,095,686 | B2 | 8/2015 | Zanne et al. | |
| 9,375,550 | B2 | 6/2016 | Tegg | |
| 9,402,604 | B2 | 8/2016 | Williams et al. | |
| 9,433,340 | B2 | 9/2016 | Jones et al. | |
| 10,667,673 | B2 | 6/2020 | Su et al. | |
| 10,881,832 | B2 | 1/2021 | Chu | |
| 2001/0004676 | A1 | 6/2001 | Ouchi | |
| 2004/0267093 | A1 | 12/2004 | Miyagi et al. | |
| 2005/0107688 | A1 * | 5/2005 | Strommer | A61B 5/7475 600/424 |
| 2005/0267327 | A1 | 12/2005 | Iizuka et al. | |
| 2007/0225754 | A1 | 9/2007 | Measamer et al. | |
| 2007/0232856 | A1 | 10/2007 | Ueno et al. | |
| 2009/0149711 | A1 | 6/2009 | Tanaka et al. | |
| 2010/0191224 | A1 | 7/2010 | Butcher | |
| 2010/0210908 | A1 | 8/2010 | Ashida et al. | |
| 2011/0263983 | A1 * | 10/2011 | Peszynski | A61B 8/445 600/443 |
| 2011/0275892 | A1 | 11/2011 | Tanaka | |
| 2014/0275763 | A1 | 9/2014 | King et al. | |
| 2014/0316203 | A1 | 10/2014 | Carroux et al. | |
| 2015/0335862 | A1 | 11/2015 | Selkee | |
| 2016/0270825 | A1 | 9/2016 | Wentz et al. | |
| 2016/0324399 | A1 | 11/2016 | Banju et al. | |
| 2017/0143195 | A1 | 5/2017 | Yee et al. | |
| 2017/0215901 | A1 | 8/2017 | Harrah et al. | |
| 2017/0273712 | A1 | 9/2017 | Carlson et al. | |
| 2019/0021707 | A1 | 1/2019 | Belsky et al. | |
| 2019/0029498 | A1 | 1/2019 | Mankowski et al. | |
| 2019/0208994 | A1 | 7/2019 | Davis | |
| 2019/0209810 | A1 | 7/2019 | Reid et al. | |
| 2019/0232027 | A1 | 8/2019 | Chu | |
| 2019/0313881 | A1 | 10/2019 | Francher | |
| 2019/0380562 | A1 | 12/2019 | Deuel et al. | |
| 2020/0054399 | A1 | 2/2020 | Duidam et al. | |
| 2020/0100647 | A1 | 4/2020 | Craig et al. | |
| 2020/0196834 | A1 | 6/2020 | Tah | |
| 2020/0345207 | A1 | 11/2020 | Nguyen et al. | |
| 2021/0045619 | A1 | 2/2021 | Sauer | |
| 2021/0045626 | A1 | 2/2021 | Hsu et al. | |
| 2021/0085153 | A1 | 3/2021 | Chu et al. | |
| 2021/0186304 | A1 | 6/2021 | Joshi et al. | |
| 2021/0186306 | A1 | 6/2021 | Komuro | |
| 2022/0079418 | A1 * | 3/2022 | Ouyang | A61B 1/0016 |
| 2022/0160207 | A1 | 5/2022 | Nycz et al. | |
| 2022/0280021 | A1 | 9/2022 | Chu | |
| 2022/0304548 | A1 | 9/2022 | Chu | |
| 2022/0362518 | A1 | 11/2022 | Gu et al. | |

FOREIGN PATENT DOCUMENTS

| | | |
|---|---|---|
| WO | 2020049718 A1 | 3/2020 |
| WO | 2020160522 A1 | 8/2020 |
| WO | 2021127426 A1 | 6/2021 |

OTHER PUBLICATIONS

Cho et al; "Evaluation of Performance Parameters of the Disposable Flexible Ureterorenoscope (LITHOVUE) in Patients with Renal Stones: A Prospective, Observational, Single-Arm, Multicenter Study," Scientific Reports, vol. 8:9795, 6 pages, Published online: Jun. 28, 2018.

Tian et al; "Cannulation Time is a More Accurate Measure of Cannulation Difficulty in Endoscopic Retrograde Cholangiopancreatography than the Number of Attempts," Gastroenterology Report, 1, pp. 193-197, Aug. 2013.

Tringali et al; "Endoscopic Retrograde Cholangiopancreatography: Indications, Patient Preparation and Complications," UpToDate®, Wolters Kluwer® 33 pages, Accessed Sep. 1, 2020.

International Search Report and Written Opinion dated Feb. 28, 2022 for International Application No. PCT/US2021/060305.

International Search Report and Written Opinion dated Jun. 10, 2022 for International Application No. PCT/US2022/018561.

Boston Scientific, Lithovue Empower™, Retrieval Deployment Device, Brochure, URO-554-002-AA, 4 pages, Jul. 2018.

International Search Report and Written Opinion dated Jun. 1, 2022 for International Application No. PCT/US2022/020951.

International Search Report and Written Opinion dated Aug. 8, 2022 for International Application No. PCT/US2022/028757.

Cotton "Income and Outcome Metrics for the Objective Evaluationn of ERCP and Alternative Methods", Gastrointestinal Endoscopy, vol. 56, No. 6, (SUPPL) pp. S283-S290, 2002.

Freeman et al., "Prevention of Post-ERCP Pancreatitis: a Comprehensive Review", Gastrointestinal Endoscopy, vol. 59, No. 7, 20 pages, 2004.

Godard et al., "Unsupervised Monocular Depth Estimation with Left-Right Consistency", Proceedings of the IEEE Conference on Computer Vision and Pattern Recognition, pp. 270-279, 2017.

Klein et al., "Parallel Tracking and Mapping for Small AR Workspaces", Active Vision Laboratory Department of Engineering Science, University of Oxford, IEEE, 10 pages, 2017.

Kowalski et al., "Perceptions of Gastroenterology Fellows Regarding ERCP Competency and Training", Gastrointestinal Endoscopy, vol. 58, No. 3, pp. 345-349, 2003.

Petersen, "ERCP Outcomes: Defining the Operators, Experience, and Environments", An Editorial, Gastrointestinal Endoscopy, vol. 55, No. 7, pp. 953-958, 2002.

Vijayakumar et al., "Locally Weighted Projection Regression: An O(n) Algorithm for Incremental Real Time Learning in High Dimensional Space", Proceedings of Seventeenth International Conference on Machine Learning (ICML2000) pp. 1079-1086, 2000. (Abstract).

Yung et al., "Muscoskeletal injuries in Gastrointestinal Endoscopists: A Systemic Review", Expert Review of Gastroenterology & Hepatology, 18 pages, 2017.

Invitation to Pay Additional Fees dated Sep. 11, 2023 for International Application No. PCT/US2023/022753.

* cited by examiner

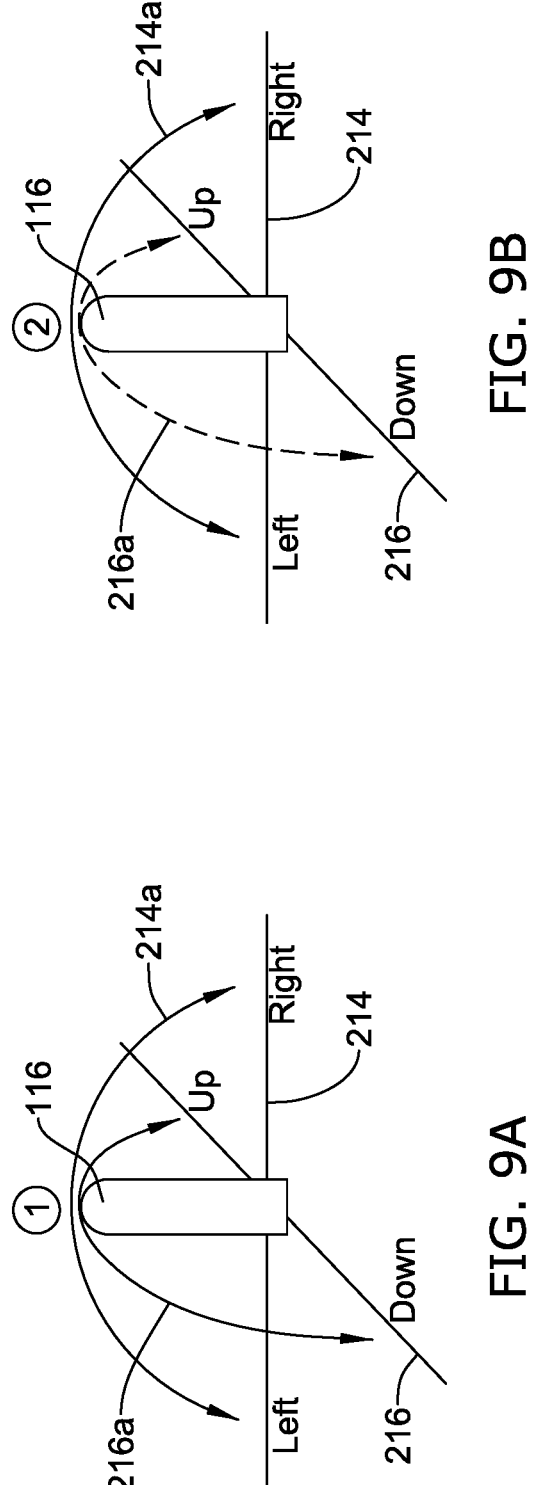
FIG. 9A
FIG. 9B
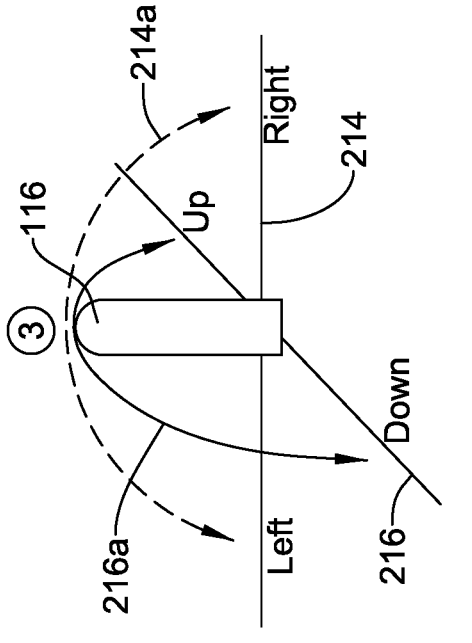
FIG. 9C

TRAJECTORY TRACKING FOR MEDICAL DEVICE

CROSS-REFERENCE TO RELATED APPLICATIONS

This application claims the benefit of U.S. Prov. Pat. App. No. 63/344,245, filed May 20, 2022, titled TRAJECTORY TRACKING FOR MEDICAL DEVICE, which is incorporated herein by reference.

TECHNICAL FIELD

The disclosure is directed to a motorized control for a medical device. More particularly, the disclosure is directed to medical device, such as an endoscope or steerable catheter, having a motor control assembly configured to provide trajectory tracking.

BACKGROUND

Medical devices, such as steerable/deflectable endoscopes and/or catheters, may be used to perform various diagnostic and/or treatment procedures. Different procedures may require different devices and/or different physical actions by the practitioner. Of the known medical devices, systems, and methods, each has certain advantages and disadvantages. There is an ongoing need to provide alternative medical devices and systems, including controls for manipulating and maneuvering such medical devices.

SUMMARY

This disclosure provides alternative medical devices and systems, including controls for manipulating and maneuvering such medical devices. An example may be found in a steerable medical device. The steerable medical device includes a handle and an elongate shaft extending distally from the handle to a distal tip, and a motor control assembly including a motor control housing configured to detachably interface with the handle. The motor control assembly includes a first drive assembly disposed within the motor control housing, a second drive assembly disposed within the motor control housing, an input device, and a controller that is operably coupled with the first drive assembly, the second drive assembly and the input device. The controller is configured to control operation of the first drive assembly and/or the second drive assembly in order to move the distal tip, to receive one or more user inputs from a user via the input device, and to modify operation of the first drive assembly and/or the second drive assembly in accordance with the received one or more inputs.

Alternatively or additionally, the first drive assembly may include a first motor and a first gear assembly operably coupled with the first motor, and the second drive assembly may include a second motor and a second gear assembly operably coupled with the second motor.

Alternatively or additionally, the steerable medical device may further include a first drive axle configured to engage the first gear assembly with a first deflection mechanism disposed within the handle, the first deflection mechanism being configured to deflect the distal tip in a first plane, and a second drive axle configured to engage the second gear assembly with a second deflection mechanism disposed within the handle, the second deflection mechanism being configured to deflect the distal tip in a second plane different from the first plane.

Alternatively or additionally, the one or more user inputs may include a command to lock out movement in either the first plane or the second plane such that when the command locks out movement in the first plane, the controller is configured to prevent the first drive assembly from moving the first deflection mechanism while the second drive assembly is permitted to move the second deflection mechanism, and when the command locks out movement in the second plane, the controller is configured to prevent the second drive assembly from moving the second deflection mechanism while the first drive assembly is permitted to move the first deflection mechanism.

Alternatively or additionally, the one or more user inputs may include a command to move the distal tip along a user-defined trajectory.

Alternatively or additionally, the user input device may be configured to allow the user to input the user-defined trajectory.

Alternatively or additionally, the controller may be further configured to operate the first drive assembly and/or the second drive assembly in order to move the distal tip along the user-defined trajectory.

Alternatively or additionally, the controller may be further configured to implement a learning model in which the controller learns how encoder values for each of the first drive assembly and the second drive assembly relate to corresponding movement of the distal tip.

Alternatively or additionally, the controller may be further configured to, when moving the first drive assembly and/or the second drive assembly, to minimize a difference between a desired encoder value and a current encoder value.

Alternatively or additionally, the one or more user inputs may include a command to move the distal tip to a user-defined target.

Alternatively or additionally, the user input device may be configured to allow the user to input the user-defined target.

Alternatively or additionally, the controller may be further configured to determine a trajectory between a current position of the distal tip and a position defined by the user-defined target, and to operate the first drive assembly and/or the second drive assembly in order to move the distal tip along the determined trajectory.

Another example may be found in a steerable medical device. The steerable medical device includes a handle and an elongate shaft extending distally from the handle to a distal tip. A first drive motor is configured to cause the distal tip to deflect within a first plane and a second drive motor is configured to cause the distal tip to deflect within a second plane different from the first plane. The steerable medical device includes an input device and a controller that is operably coupled with the first drive motor, the second drive motor and the input device. The controller is configured to receive instructions to move the distal tip along a trajectory, implement a learning model that indicates how encoder values for each of the first motor and the second motor correspond to movement of the distal tip, and control operation of the first drive motor and/or the second drive motor in order to move the distal tip along the trajectory while minimizing a difference between a desired encoder value and a current encoder value.

Alternatively or additionally, the trajectory may include a user-defined trajectory inputted to the controller.

Alternatively or additionally, the input device may be configured to allow the user to input the user-defined trajectory.

Alternatively or additionally, the trajectory may include a controller-determined trajectory that is based upon a current position of the distal tip and a desired target location of the distal tip.

Alternatively or additionally, the controller may be further configured to determine whether the target location of the distal tip is reachable given a current location of the steerable medical device.

Alternatively or additionally, the controller may be further configured to automatically calculate the controller-determined trajectory when the target location of the distal tip is reachable given the current location of the steerable medical device, and to provide provides instructions to the user to move the steerable medical device to a new location that will facilitate reaching the target location of the distal tip when the target location of the distal tip is not reachable given the current location of the steerable medical device.

Alternatively or additionally, the controller may be further configured to estimate a depth of the target location.

Another example may be found in a steerable medical device. The steerable medical device includes a handle and an elongate shaft extending distally from the handle to a distal tip. A first drive motor is configured to cause the distal tip to deflect in a first plane and a second drive motor is configured to cause the distal tip to deflect in a second plane different from the first plane. The steerable medical device includes an input device and a controller that is operably coupled with the first drive motor, the second drive motor and the input device. The controller is configured to control operation of the first drive motor and/or the second drive motor in order to move the distal tip. The controller is configured to receive a command to restrict movement along either the first plane or the second plane. When the command locks out movement in the first plane, the controller is configured to prevent the first drive motor from causing movement along the first plane while permitting movement along the second plane. When the command locks out movement in the second plane, the controller is configured to prevent the second drive motor from causing movement along the second plane while permitting movement along the first plane.

The above summary of some embodiments, aspects, and/or examples is not intended to describe each embodiment or every implementation of the present disclosure. The Figures and the detailed description which follows more particularly exemplify these embodiments.

BRIEF DESCRIPTION OF THE DRAWINGS

The disclosure may be more completely understood in consideration of the following detailed description in connection with the accompanying drawings, in which:

FIGS. 9A, 9B and 9C illustrate distal tip motion modes that may be implemented by the illustrative motorized control unit of FIG. 7;

Figure 1:
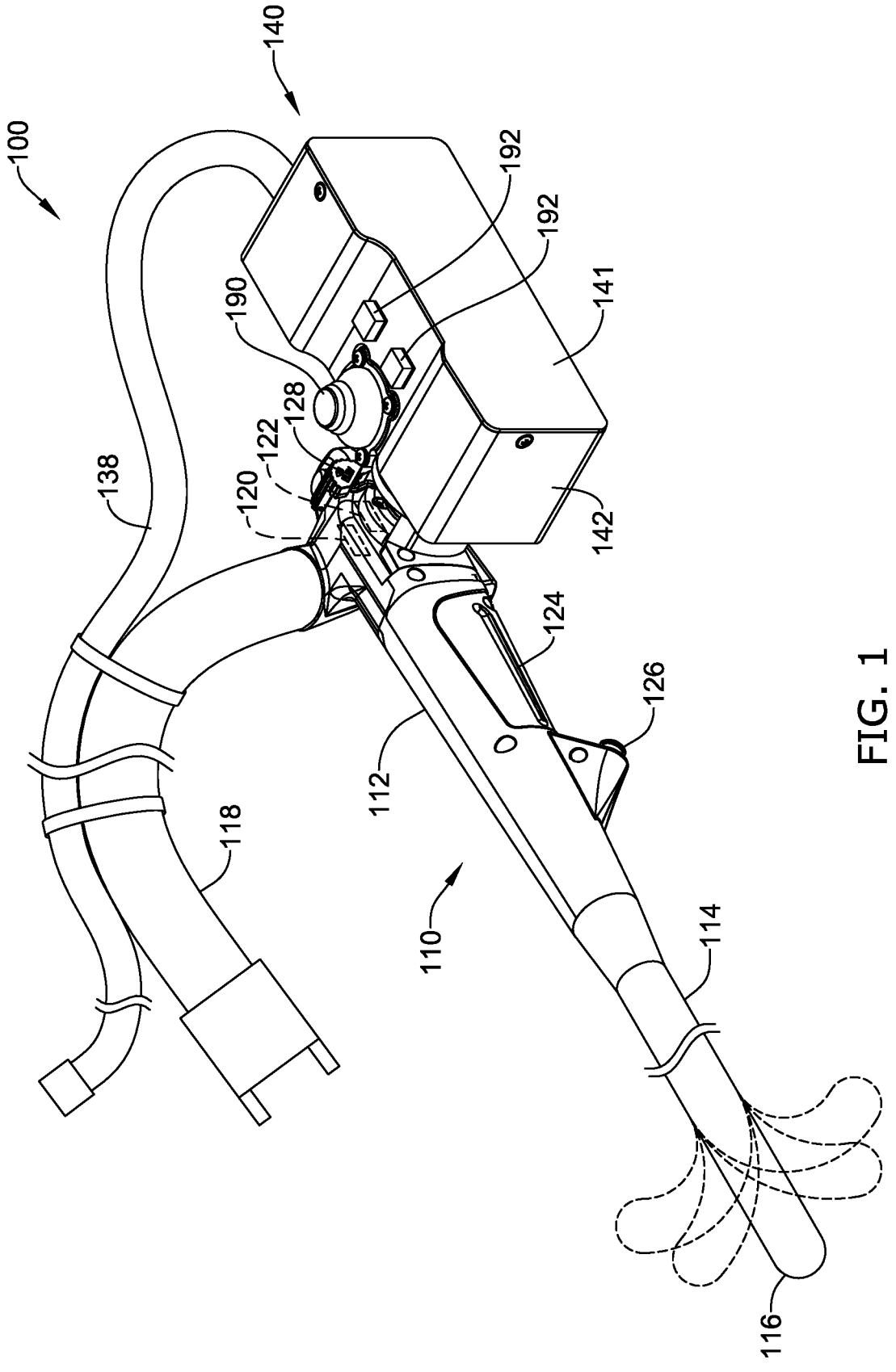
FIG. 1 is a perspective view of an illustrative endoscope system.

While the embodiments of the present disclosure are amenable to various modifications and alternative forms, specifics thereof have been shown by way of example in the drawings and will be described in detail. It should be understood, however, that the intention is not to limit aspects of the present disclosure to the particular embodiments described. On the contrary, the intention is to cover all modifications, equivalents, and alternatives falling within the spirit and scope of the present disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claims. Those skilled in the art will recognize that the various elements described and/or shown may be arranged in various combinations and configurations without departing from the scope of the disclosure. The detailed description and drawings illustrate example embodiments. However, in the interest of clarity and ease of understanding, while every feature and/or element may not be shown in each drawing, the feature(s) and/or element(s) may be understood to be present regardless, unless otherwise specified.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant Figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the embodiments of the present disclosure are necessarily shown in each Figure or discussed in detail below. However, it will be understood that the following discussion may apply equally to any and/or all of the components for which there are more than one, unless explicitly stated to the contrary. Additionally, not all instances of some elements or features may be shown in each Figure for clarity.

Relative terms such as "proximal", "distal", "advance", "retract", variants thereof, and the like, may be generally considered with respect to the positioning, direction, and/or operation of various elements relative to a user of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to affect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

Some medical/surgical procedures—for example: kidney stone management, ERCP (endoscopic retrograde cholangiopancreatography), pulmonary biopsy, colonoscopy, bladder mapping, cardiac mapping, cardiac valve replacement and/or repair, and others—may require navigation of an elongate shaft of a medical device through tortuous anatomy to position the elongate shaft, such as the distal tip of the elongate shaft, of the medical device(s) at a specific location and/or orientation. Some of these procedures may be long and/or may involve difficult physical actions that may lead to physician fatigue and/or musculoskeletal injury. In some medical/surgical procedures, the physician may be at risk of work-related strain due to repetitive motions, prolonged awkward posture(s), high forces, contact stress, and/or vibration. For example, some physicians may be at risk to develop De Quervain's tenosynovitis (swelling and pain at the base of the thumb), carpal tunnel syndrome, ganglion cysts, "trigger finger", and/or other conditions. In some instances, a physician's hand size may negatively affect his or her ability to control the medical device and/or perform medical/surgical procedures. The current disclosure relates to features that may reduce and/or eliminate physician fatigue resulting from the procedure(s), may improve usability and/or ergonomics of the medical device for varying hand sizes, may provide more precision and/or more precise movements and stability when using the medical device, and may make using the medical device and/or performing certain procedures easier to learn.

FIGS. 1-6 illustrate various features of an illustrative endoscope system 100. In some embodiments, the endoscope system 100 may include an endoscope 110. The endoscope 110 may be specific to a particular endoscopic procedure, such as, e.g., a ureteroscope, a cystoscope, a nephroscope, a duodenoscope, etc., or may be a general-purpose device suitable for a wide variety of procedures. In some embodiments, the endoscope 110 includes a handle 112 and an elongate shaft 114 extending distally from the handle 112 to a distal tip 116, wherein the handle 112 includes a first deflection mechanism 120 configured to deflect and/or articulate the distal tip 116 of the elongate shaft 114 in a first plane and a second deflection mechanism 122 configured to deflect and/or articulate the distal tip 116 of the elongate shaft 114 in a second plane different from the first plane. In some embodiments, the first plane may be oriented at a non-zero angle to the second plane. In some embodiments, the first plane may be oriented perpendicular to the second plane. As an example, the first plane may correspond to up and down while the second plane may correspond to left and right. It will be appreciated that this is merely illustrative, and of course depends at least in part upon the particular orientation of the endoscope 100. Other configurations are also contemplated. Although depicted as an endoscope system 100 including an endoscope 110, it is noted and understood that features, components, and/or functionality described herein may be incorporated into another medical device, such as a steerable catheter or other medical device having one or more deflection mechanisms for controlling deflection and/or articulation of a distal tip of the elongate shaft of the medical device to facilitate navigation of the elongate shaft through the anatomy of a patient. Accordingly, the described components such as the handle, elongate shaft, deflection mechanisms, motor control assembly, and other components may be associated with another medical device having a deflectable/steerable distal tip of an elongate shaft, as desired.

In some embodiments, the first deflection mechanism 120 may include a first pulley or rotating member disposed within the handle 112 and operatively connected to the distal tip 116. In some embodiments, one or more first cables, wires, or other filaments may be engaged with and/or connected to the first pulley within the handle 112. In some embodiments, the one or more first cables, wires, or filaments may be engaged with and/or connected to the distal tip 116, such that tension applied to the one or more first cables, wires, or filaments by the first pulley deflects and/or articulates the distal tip 116 in the first plane. In some embodiments, the second deflection mechanism 122 may include a second pulley or rotating member disposed within the handle 112 and operatively connected to the distal tip 116. In some embodiments, one or more second cables, wires, or other filaments may be engaged with and/or connected to the second pulley within the handle 112. In some embodiments, the one or more second cables, wires, or filaments may be engaged with and/or connected to the distal tip 116, such that tension applied to the one or more second cables, wires, or filaments by the second pulley deflects and/or articulates the distal tip 116 in the second plane. Other configurations are also contemplated.

Figure 2:
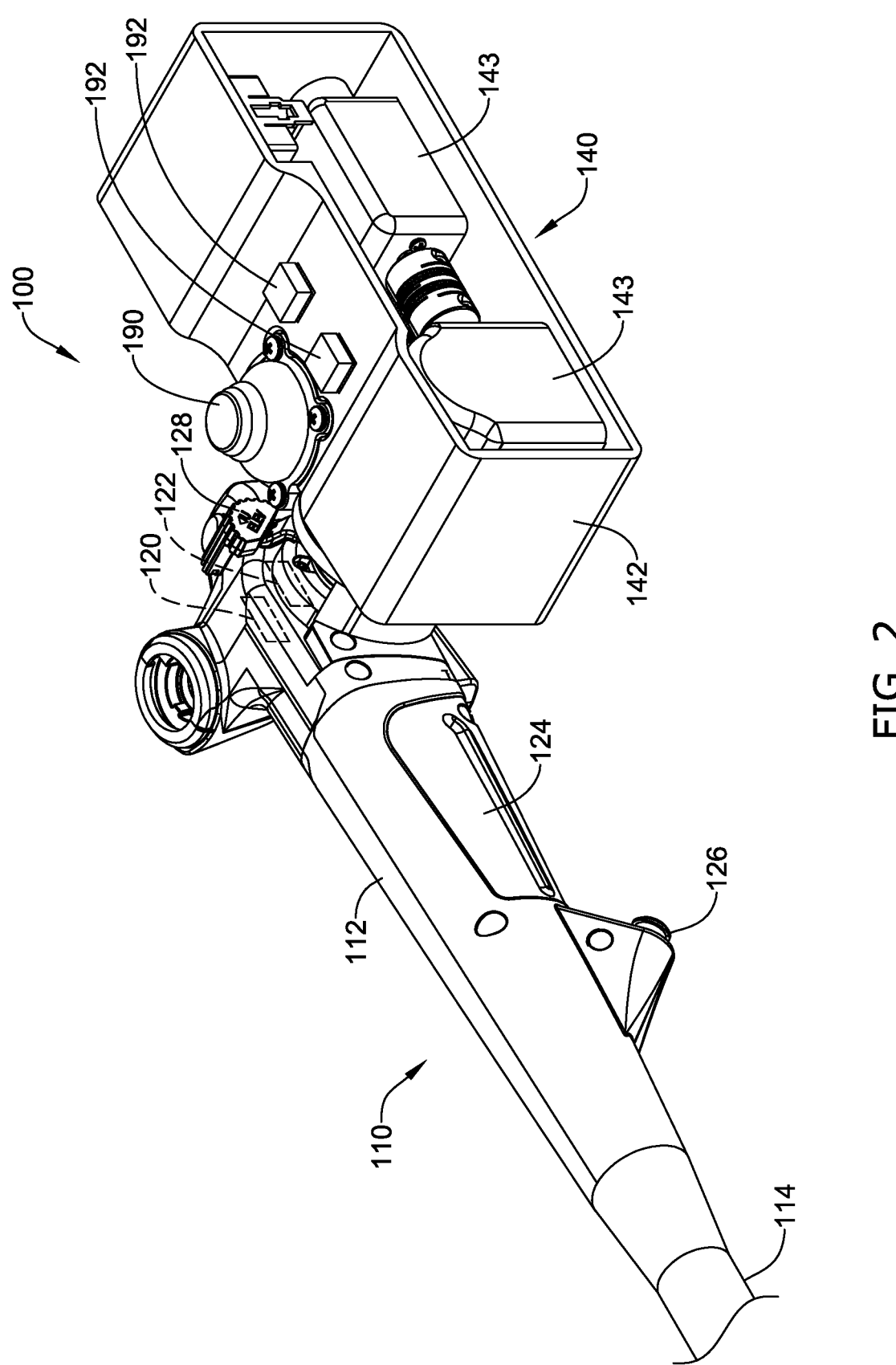
FIG. 2 is a perspective view of the illustrative endoscope system of FIG. 1 with a portion of a housing removed.
Figure 3:
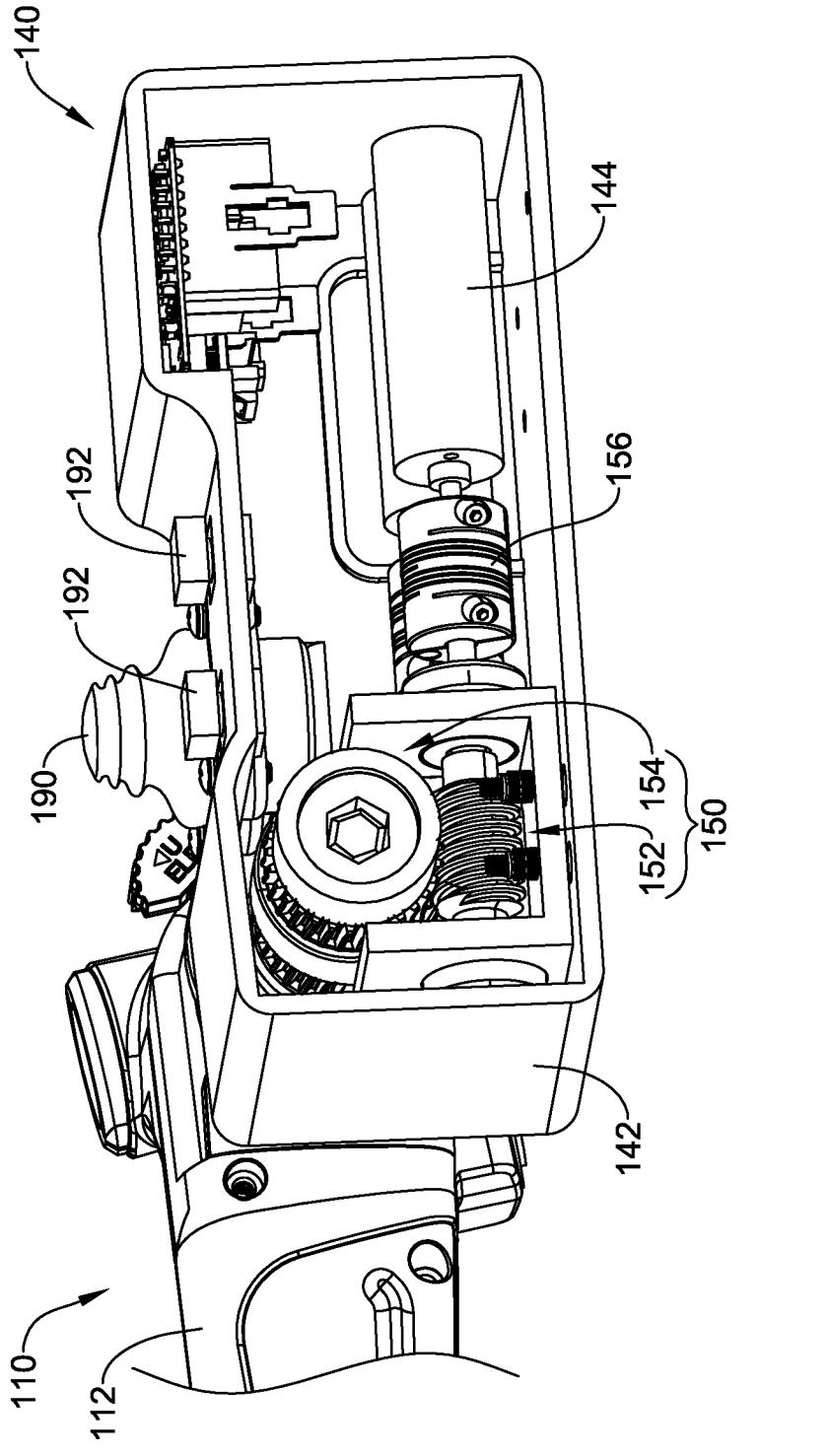
FIG. 3 is a perspective view of the illustrative endoscope system of FIG. 1 with a portion of a housing removed.

As such, in some embodiments, the endoscope system 100 may include a motor control assembly 140 including a motor control housing 142 configured to detachably interface with the handle 112 of the endoscope 110. In some embodiments, the motor control housing 142 may include a removable cover 141 (e.g., FIG. 1), wherein internal components of the motor control assembly 140 may be accessed after removing the removable cover 141, as seen in FIG. 2. Additionally, in some embodiments, the motor control assembly 140 may include one or more internal covers 143 disposed within the motor control housing 142 that may protect certain components and/or groups of components from each other, contamination, etc. In some embodiments, the one or more internal covers 143 may provide structural support for selected internal components. In FIG. 3, the one or more internal covers 143 have been removed to facilitate discussion related to selected internal components of the motor control assembly 140. It shall be understood that the presence and/or use of all, some, or any of the one or more internal covers 143 is optional and is not required.

Figure 4:
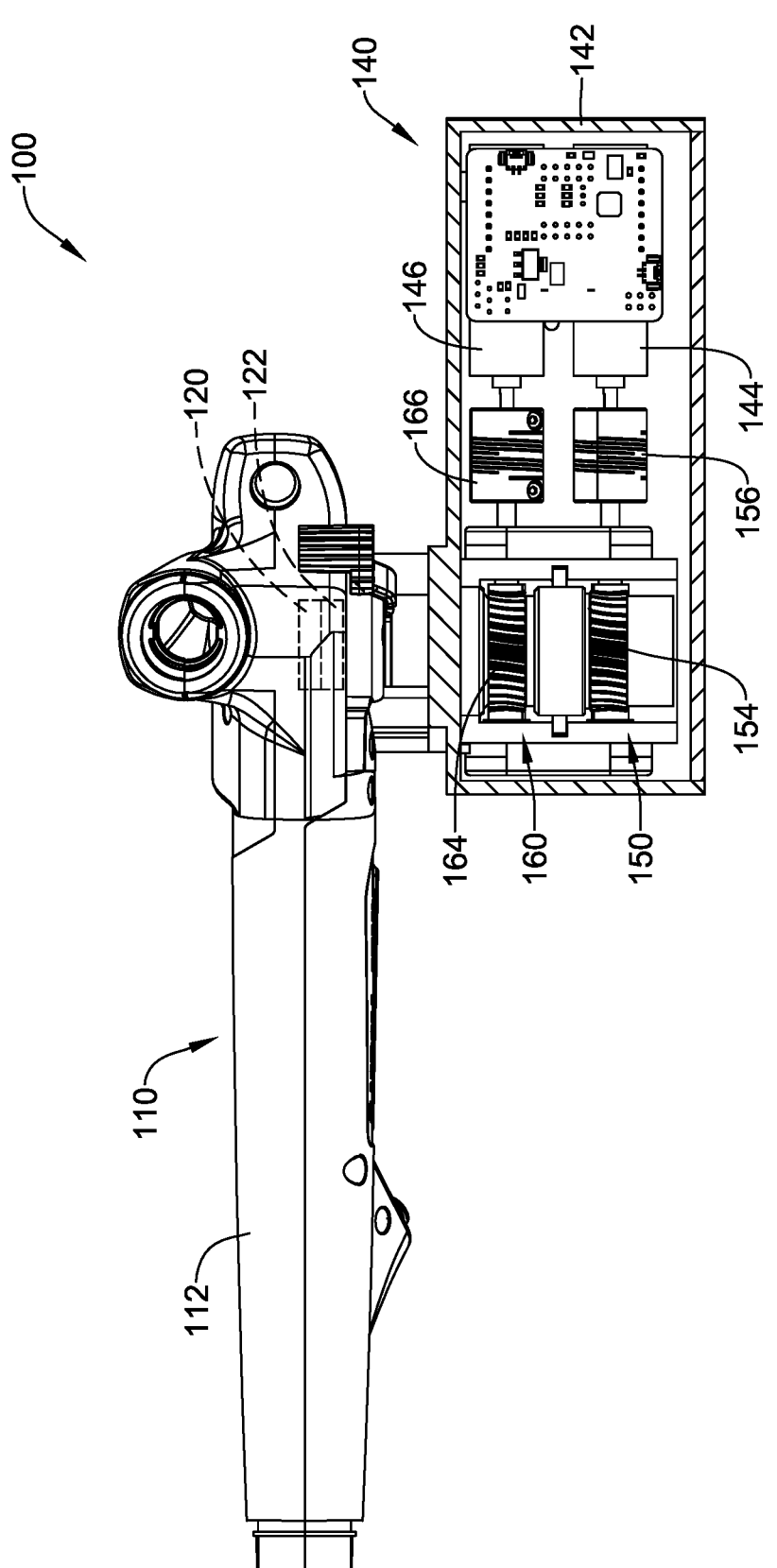
FIG. 4 is a side view of the illustrative endoscope system of FIG. 1 with a portion of a housing removed.
Figure 5:
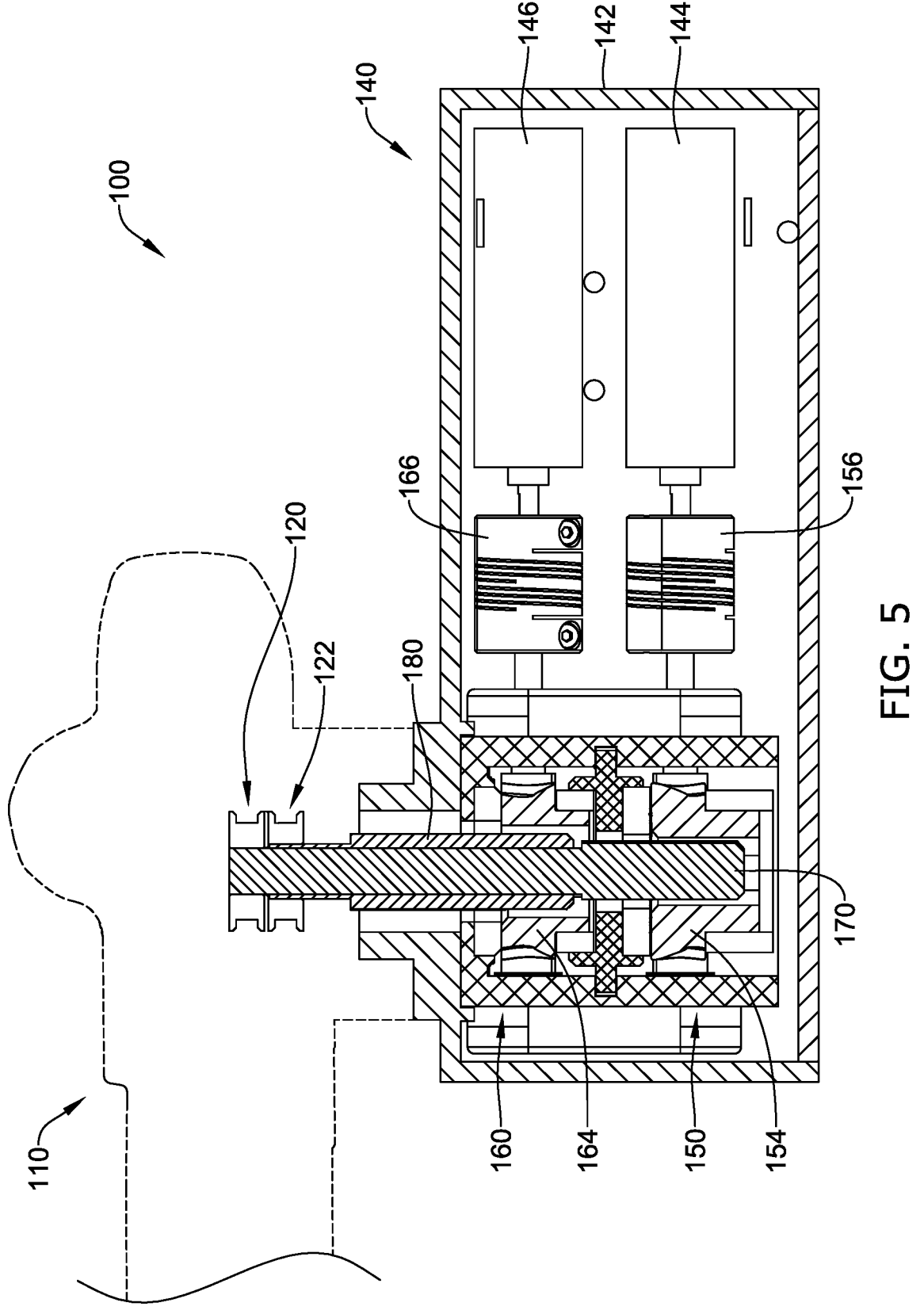
FIG. 5 is a side view of the illustrative endoscope system of FIG. 1 with a portion of a housing removed.

In some embodiments, the motor control assembly 140 may include at least one motor (e.g., FIGS. 3-5) disposed within the motor control housing 142. In some embodiments, the at least one motor may include a first motor 144 disposed within the motor control housing 142, as seen in FIG. 3. In some embodiments, the at least one motor may include a second motor 146 disposed within the motor control housing 142, as seen in FIGS. 4 and 5. In some embodiments, the at least one motor may include the first motor 144 disposed within the motor control housing 142 and the second motor 146 disposed within the motor control housing 142. In some embodiments, for each controlled degree of freedom of the distal tip 116, an individual motor may be added to the at least one motor.

The at least one motor may be electric and may be brushed or brushless DC motors. The at least one motor may provide the user partial force assistance for deflecting the distal tip 116, from 0% to 100% force assistance, thereby allowing for fully manual control, assisted control with reduced lever/knob force, or fully actuated control. Each motor may be attached to a rotary encoder which provides a relative position of said motor to a controller that at least partially regulates operation of each motor. As will be discussed with respect to FIG. 7, the motor control assembly 140 may include a motorized control unit 200. In some embodiments, additional inputs for the CPU, the microprocessor, and/or the combination thereof may include components of the user interface, tactile feedback electronics, etc.

In some embodiments, the motor control assembly 140 may include a user input mechanism. In some embodiments, the user input mechanism may include one or more of a joystick control, a scroll wheel, a knob, a slider, a keypad, a touch screen interface or control, a voice interface or control, etc. The user input mechanism may, for example, be operably coupled with the motorized control unit 200 that will be discussed with respect to FIG. 7. Returning briefly to FIGS. 1-3, in some embodiments, the motor control assembly 140 may include a joystick control 190 configured to operate the at least one motor disposed within the motor control housing 142. In some embodiments, the joystick control 190 may be configured to operate the first motor 144. In some embodiments, the joystick control 190 may be configured to operate the second motor 146. In some embodiments, the joystick control 190 may be configured to operate the first motor 144 and the second motor 146. In some embodiments, the joystick control 190 may be configured to operate the first motor 144 and the second motor 146 simultaneously. In some embodiments, the joystick control 190 may be configured to operate the first motor 144 and the second motor 146 independently of each other. Other configurations are also contemplated.

In some embodiments, the motor control assembly 140 may include a homing feature configured to return the distal tip 116 to a home position (e.g., to a straightened and/or non-deflected configuration) and/or a speed control feature configured to control speed and/or responsiveness of movement of the distal tip 116. In some embodiments, the homing feature and/or the speed control feature may each include an input mechanism. For example, the input mechanism may be one or more buttons, a voice interface and/or control, a gesture interface and/or control, or other suitable means of providing input to the motor control assembly 140 and/or the user interface.

In some embodiments, the motor control assembly 140 may include one or more buttons 192. In some embodiments, the one or more buttons 192 may include a first button (e.g., a home button) configured to return the distal tip 116 to the home position (e.g., to the straightened configuration), wherein activation of the first button automatically actuates the at least one motor to move the distal tip 116 to the home position. In some embodiments, the one or more buttons 192 may include a second button that is user configurable to retain a saved position or configuration, wherein activation of the second button automatically actuates the at least one motor to move the distal tip 116 to the saved position and/or configuration. Additional buttons and/or other configurations are also contemplated. Additionally, while the one or more buttons 192 are discussed herein by way of example, the motor control assembly 140 is not limited to the use of physical buttons and may include other input mechanisms.

In some embodiments, the motor control assembly 140 may include a self-homing feature and/or procedure. In one example, upon connecting the motor control assembly 140 to the handle 112, a homing program and/or algorithm is activated and/or run for the first motor 144 and the second motor 146 (where present) sequentially (e.g., the procedure is done on the first motor 144 and then is done on the second motor 146). In some instances, the homing program and/or algorithm is automatically initiated by the motorized control unit 200 (FIG. 7) when the motor control assembly 140 is connected to the handle 112. In other instances, the user may push a button, or otherwise manually initiate the homing program and/or algorithm after the motor control assembly 140 is connected to the handle 112. The first motor 144 may start rotating in a first direction while the current is being monitored by the homing program and/or algorithm. Upon registering, encountering, and/or identifying a sudden increase in the amount of current drawn by the first motor 144, a location of an encoder is saved as a checkpoint for an upper limit or a lower limit. The first motor 144 then starts turning in a second direction opposite the first direction and again upon registering, encountering, and/or identifying a sudden increase in the amount of current drawn by the first motor 144, the value of the encoder is saved as a second checkpoint for the other limit of the motion range for that axis and/or the first motor 144. After determining the upper limit and the lower limit of the first motor 144 (and finding their corresponding values in terms of encoder values) the algorithm may divide the number of ticks between the upper limit and the lower limit by two. The corresponding encoder value would be the middle of the motion range or the home position for that axis and/or the first motor 144.

The same procedure is then repeated for the second motor 146, wherein the second motor 146 may start rotating in the first direction while the current is being monitored by the homing program and/or algorithm. Upon registering, encountering, and/or identifying a sudden increase in the amount of current drawn by the second motor 146, a location of an encoder is saved as a checkpoint for an upper limit or a lower limit. The second motor 146 then starts turning in the second direction opposite the first direction and again upon registering, encountering, and/or identifying a sudden increase in the amount of current drawn by the second motor 146, the value of the encoder is saved as a second checkpoint for the other limit of the motion range for that axis and/or the second motor 146. After determining the upper limit and the lower limit of the second motor 146 (and finding their corresponding values in terms of encoder values) the algorithm may divide the number of ticks between the upper limit and the lower limit by two. The corresponding encoder value would be the middle of the motion range or the home position for that axis and/or the second motor 146.

In another example, the homing feature and/or procedure may be manually activated after engaging the motor control assembly 140 to the handle 112 of the endoscope 110. Other configurations are also contemplated.

In some embodiments, the joystick control 190 may be configured to control movement of the distal tip 116. In some embodiments, the joystick control 190 may be configured to control a speed at which the distal tip 116 moves and/or responsiveness of the joystick control 190. In some embodiments, the motor control assembly 140 may include a speed change control button. In some embodiments, the speed change control button may be built into and/or may be integrated into the joystick control 190. For example, in some embodiments, pressing axially on the joystick control 190 toward the motor control housing 142 may actuate the speed change control button. The speed change control feature and/or the speed change control button may actuate and/or cycle through a plurality of speed settings to permit at least some degree of customization over the speed and/or responsiveness of movement of the distal tip 116. In some embodiments, the plurality of speed settings may include at least a high speed setting which permits faster control and/or faster movement of the distal tip 116 and a low speed setting which permits finer control and/or slower movement of the distal tip 116. In some embodiments, the plurality of speed settings may further include a medium speed setting and/or other speed settings (e.g., medium-high, medium-low, extra low, etc.).

In some embodiments, the motor control housing 142, the speed change control feature, the speed change control button, and/or the plurality of speed settings may be user customizable. In some embodiments, the user may be able to set speed mode(s), select and/or set desired speed(s), and/or set or save the speed mode(s) and/or desired speed(s). In some embodiments, the speed change control button may be depressed and held to set or save the speed mode(s) and/or desired speed(s). In some embodiments, the motor control housing 142 and/or the user interface may include additional buttons, a keypad, a scroll wheel, a dial, a touch interface, or other input mechanism for setting and/or adjusting the speed mode(s) and/or desired speed(s). These are only examples, and other configurations are also contemplated.

In some embodiments, other control mechanisms may be used in place of the joystick control 190. In some embodiments, the motor control assembly 140 may include a keypad. In some embodiments, the motor control assembly 140 may include a scroll wheel. In some embodiments, the motor control assembly 140 may include a touch screen. Other control configurations are also contemplated.

In some embodiments, the distal tip 116 may include a camera and may, for example, have deflection and/or articulation capabilities in one or more directions for viewing patient anatomy. In some embodiments, the endoscope 110 may be a duodenoscope such as an Exalt™ Model D scope. However, other medical devices, such as another endoscope (e.g., a ureteroscope, etc.) or related system, (e.g., Lithovue™ SpyScope™ DS, SpyGlass™ DS, etc.) may be used in addition to or in place of a duodenoscope and/or the endoscope 110. In some embodiments, the endoscope 110 may be configured to deliver fluid from a fluid management system to a treatment site via the elongate shaft 114. The elongate shaft 114 may include one or more working lumens for receiving a flow of fluid and/or other medical devices therethrough. In some embodiments, the endoscope 110 may be connected to the fluid management system via one or more supply line(s).

In some embodiments, the handle 112 of the endoscope 110 may include a plurality of elements configured to facilitate the endoscopic procedure. In some embodiments, an umbilicus 118 extends from the handle 112 and is configured for attachment to an electronic device (not pictured) such as e.g. a computer system, a console, a microcontroller, etc. for providing power, analyzing endoscopic data, controlling the endoscopic intervention, and/or performing other functions. In some embodiments, the electronic device to which the umbilicus 118 is connected may have functionality for recognizing and exchanging data with other endoscopic accessories. The handle 112 may include a grip area 124 for the operating physician to grasp while performing the endoscopic procedure. In some embodiments, the handle 112 may include a side port 126 in communication with the one or more working lumens of the elongate shaft 114 and/or the endoscope 110.

In some embodiments, a motor control umbilicus 138 may extend from the motor control housing 142 and may be configured for attachment to an electronic device, which may be the same electronic device that the umbilicus 118 is attached to or may be a different electronic device as desired, for providing power, controlling endoscopic intervention and/or the motor control assembly, and/or other functions. In some embodiments, the motor control umbilicus 138 may be secured to the umbilicus 118. In some embodiments, the motor control umbilicus 138 may be releasably and/or removably secured to the umbilicus 118. In some embodiments, the motor control umbilicus 138 may be secured to the umbilicus 118 with a hook and loop closure device (e.g., Velcro™), tape, a wire tie, or other securement apparatus.

In some embodiments, the endoscope 110 may be in electronic communication with a workstation via a wired connection (e.g., the umbilicus 118). In some embodiments, the workstation may include a touch panel computer, an interface box for receiving the wired connection (e.g., the umbilicus 118), a cart, and a power supply, among other features. In some embodiments, the interface box may be configured with a wired or wireless communication connection with the controller of the fluid management system. The touch panel computer may include at least a display screen and an image processor. In some embodiments, the workstation may be a multi-use component (e.g., used for more than one procedure) while the endoscope 110 may be a single use device, although this is not required. In some embodiments, the workstation may be omitted and the endoscope 110 may be electronically coupled directly to the controller of a fluid management system, where used.

In some embodiments, the handle 112 may include at least one communication interface for attaching accessory devices. In some embodiments, the handle 112 may include Universal Serial Bus type-C (USB-C) ports, Universal Serial Bus (USB) ports, ethernet ports, and/or other types of ports. In some embodiments, more, less, and/or other communication interfaces of various types, including, for example, custom interfaces, may be used. In some embodiments, the handle 112 has only one communication interface but may be connectable to e.g. a USB hub with multiple ports for connecting multiple accessories. In some embodiments, the at least one communication interface may provide power to the accessory device(s) in addition to exchanging data therewith. Thus, the accessory device(s) need not have separate cables running to a connected electronic device or a battery that adds additional weight to the handle 112. In some embodiments, the accessory device(s) may be uniquely associated with the endoscope 110 and recognized by the electronic device through "plug and play" functionality without any user setup required.

In some embodiments, the endoscope 110 may include one or more sensors proximate the distal tip 116 and/or the distal end of the elongate shaft 114. For example, the endoscope 110 may include a pressure sensor at the distal tip 116 of the elongate shaft 114 to measure intracavity pressure within the treatment site. The endoscope 110 may also include other sensors such as, for example, a temperature sensor, a Fiber Bragg grating optical fiber to detect stresses, and/or an antenna or electromagnetic sensor (e.g., a position sensor). In some embodiments, the distal tip 116 and/or the distal end of the endoscope 110 may also include at least one camera to provide a visual feed to the user on the display screen of the touch panel computer. In another embodiment, the endoscope 110 may include two cameras having different communications requirements or protocols so that different information may be relayed to the user by each camera. When so provided, the user may switch back and forth between the cameras at will through the touch screen interface and/or the touch panel computer. While not explicitly shown, the elongate shaft 114 may include one or more working lumens for receiving the fluid and/or other medical devices. In some embodiments, the distal tip 116 may include an elevator configured to manipulate a guidewire, a tool, a medical instrument, etc. extending through the elongate shaft 114. The handle 112 may include an elevator control 128 operably connected to the elevator. In some embodiments, the at least one motor may include a motor configured to control and/or power movement of the elevator. In some embodiments, an elevator motor may be disposed within the handle 112 of the endoscope 110.

In some embodiments, the location of the distal tip 116 and/or the distal end of the elongate shaft 114 may be tracked during use. For example, a mapping and navigation system may include an operating table (or other procedural or examination table or chair, etc.) configured to act or function as an electromagnetic generator to generate a magnetic field of a known geometry. Alternatively, or additionally, an electromagnetic generator separate from the operating table may be provided. The operating table and/or the electromagnetic generator may be operatively coupled to a control unit which may include among other features, a processor, a memory, a display, and an input means. A position sensor (e.g., the electromagnetic sensor, etc.) or antenna, may be incorporated into the distal tip 116 and/or the distal end of the elongate shaft 114 of the endoscope 110. The position sensor may be configured for use in sensing a location of the position sensor in the magnetic field of the mapping and navigation system. In some embodiments, the position sensor may be electronically coupled to the workstation. When the position sensor is in the magnetic field, the location of the position sensor can be mathematically determined relative to the electromagnetic field source (e.g., the operating table and/or the electromagnetic generator). The workstation and the control unit may communicate to determine the position of the position sensor relative to the patient.

In some embodiments, the motor control assembly 140 may include a first gear assembly 150 disposed within the motor control housing 142, as seen in FIGS. 3 and 4. In some embodiments, the first gear assembly 150 may include a first worm gear 154 and a first worm gear shaft 152 configured to engage the first worm gear 154. In some embodiments, the first worm gear shaft 152 may be coupled to the first motor 144 by a first motor coupler 156. In some embodiments, the first worm gear shaft 152 may be coupled directly to the first motor 144. Other configurations are also contemplated. In some embodiments, the motor control assembly 140 may include a second gear assembly 160 disposed within the motor control housing 142, as seen in FIGS. 4 and 5. In some embodiments, the second gear assembly 160 may include a second worm gear 164 and a second worm gear shaft (not visible) configured to engage the second worm gear 164. In some embodiments, the second worm gear shaft may be coupled to the second motor 146 by a second motor coupler 166. In some embodiments, the second worm gear shaft may be coupled directly to the second motor 146. Other configurations are also contemplated. In some embodiments, the motor control assembly 140 may include the first gear assembly 150 and the second gear assembly 160 disposed within the motor control housing 142.

In some embodiments, the endoscope system 100 may include a first drive axle 170 extending from the first gear assembly 150 to the first deflection mechanism 120 disposed within the handle 112, as seen in FIGS. 4 and 5. In some embodiments, the first drive axle 170 may be configured to engage the first gear assembly 150 with the first deflection mechanism 120 disposed within the handle 112. In some embodiments, the first drive axle 170 may be configured to slidably engage the first gear assembly 150. In some embodiments, the first drive axle 170 may be fixedly secured to the first deflection mechanism 120.

In some embodiments, the endoscope system 100 may include a second drive axle 180 extending from the first gear assembly 150 to the first deflection mechanism 120 disposed within the handle 112, as seen in FIGS. 4 and 5. In some embodiments, the second drive axle 180 may be configured to engage the second gear assembly 160 with the second deflection mechanism 122 disposed within the handle 112. In some embodiments, the second drive axle 180 may be configured to slidably engage the second gear assembly 160. In some embodiments, the second drive axle 180 may be fixedly secured to the second deflection mechanism 122.

In some embodiments, the first drive axle 170 may be oriented parallel with the second drive axle 180. In some embodiments, the first drive axle 170 may be coaxially disposed with respect to the second drive axle 180, as seen in FIG. 5. In some embodiments, a first portion of the first drive axle 170 may include a circular cross-sectional shape and a second portion of the first drive axle 170 may include a non-circular cross-sectional shape (e.g., polygonal, oblong, triangular, square, star shaped, hex shaped, etc.). The second portion of the first drive axle 170 may be configured to engage with the first worm gear 154. In some embodiments, the first drive axle 170 may be non-rotatable with respect to the first worm gear 154. Other configurations are also contemplated.

In some embodiments, a first portion of the second drive axle 180 may include a circular cross-sectional shape and a second portion of the second drive axle 180 may include a non-circular cross-sectional shape (e.g., polygonal, oblong, triangular, square, star shaped, hex shaped, etc.). The second portion of the second drive axle 180 may be configured to engage with the second worm gear 164. In some embodiments, the second drive axle 180 may be non-rotatable with respect to the second worm gear 164. Other configurations are also contemplated.

In some embodiments, the first portion of the first drive axle 170 may be disposed within the lumen of the second drive axle 180. Accordingly, in some embodiments, at least a portion of the first drive axle 170 may be coaxially disposed within the lumen of the second drive axle 180. The first drive axle 170 may be rotatable relative to the second drive axle 180. As such, the first drive axle 170 and the second drive axle 180 may be rotatable independently of each other. For example, in some embodiments, the first drive axle 170 may rotate and the second drive axle 180 may remain stationary. In some embodiments, the second drive axle 180 may rotate and the first drive axle 170 may remain stationary. In some embodiments, the first drive axle 170 may rotate in a first direction and the second drive axle 180 may rotate in a second direction, wherein the second direction may be the first direction, or the second direction may be different from the first direction. In some embodiments, the first drive axle 170 may rotate at a different speed from the second drive axle 180.

Figure 6:
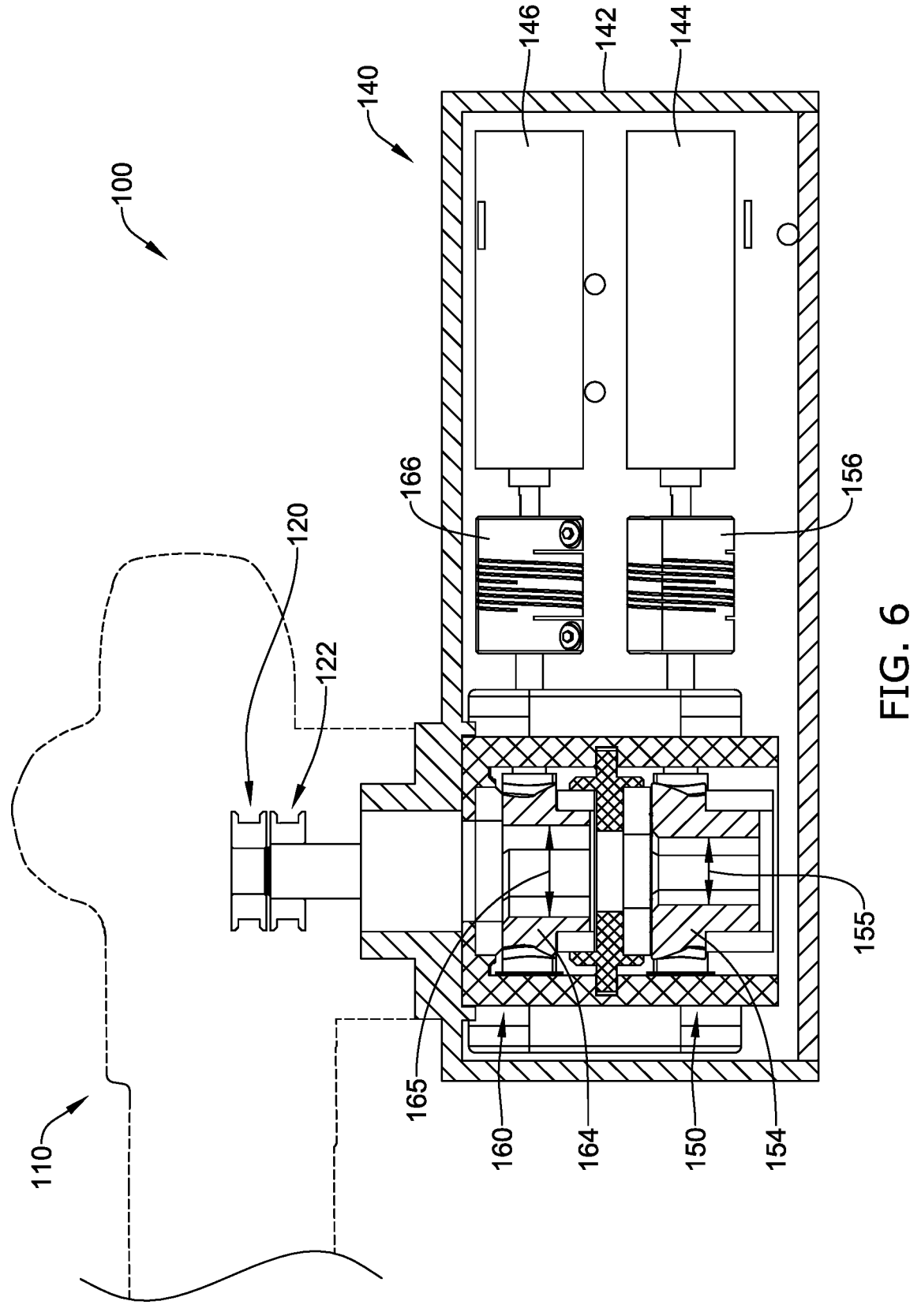
FIG. 6 is a side view of the illustrative endoscope system of FIG. 1 with a portion of a housing removed.

In some embodiments, the first drive axle 170 may define a first maximum outer extent and the second drive axle 180 may define a second maximum outer extent, wherein the second maximum outer extent is greater than the first maximum outer extent, as seen in FIG. 5. Accordingly, the first worm gear 154 may define a first maximum inner extent 155 and the second worm gear 164 may define a second maximum inner extent 165, wherein the second maximum inner extent 165 is greater than the first maximum inner extent 155, as seen in FIG. 6. Additional details regarding the exemplary medical device, depicted as an endoscope system 100, may be found in U.S. Provisional Patent Application Ser. No. 63/187,988, filed May 13, 2021 and entitled MOTORIZED CONTROL FOR MEDICAL DEVICE, and U.S. patent application Ser. No. 17/741,887, filed May 11, 2022 and entitled MOTORIZED CONTROL FOR MEDICAL DEVICE; which applications are incorporated by reference herein.

Figure 7:
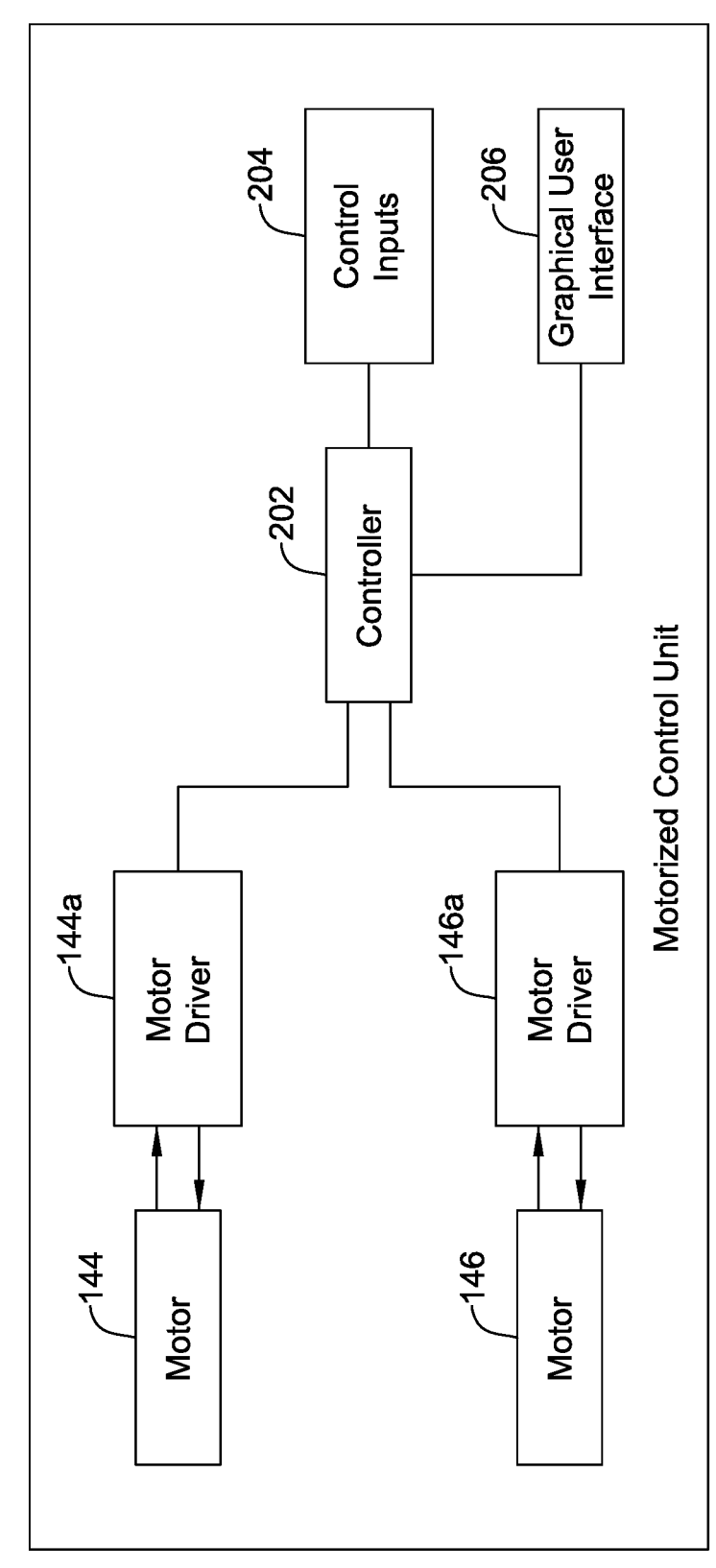
FIG. 7 is a schematic block diagram of an illustrative motorized control unit usable with the illustrative endoscope system of FIG. 1.

FIG. 7 is a schematic block diagram of the illustrative motorized control unit 200. It will be appreciated that the motorized control unit 200 may be incorporated into the motor control assembly 140. As can be seen, the motorized control unit 200 includes the first motor 144 and the second motor 146. In some embodiments, the first motor 144 is operably coupled with a first motor driver 144a. In some embodiments, the second motor 146 is operably coupled with a second motor driver 146a. The first motor driver 144a and the second motor driver 146a may, for example, be configured to have bi-directional communication with the first motor 144 and the second motor 146, respectively. In some embodiments, the first motor driver 144a and the second motor driver 146a may receive motor position information from the first motor 144 and the second motor 146, respectively. As an example, the first motor 144 and the second motor 146 may each include a quadrature encoder that provides information regarding exact motor position of the first motor 144 and the second motor 146 to the first motor driver 144a and the second motor driver 146a, respectively. The quadrature encoders may be considered as being examples of the rotary encoders referenced previously with respect to the motor control assembly 140. In some embodiments, the first motor driver 144a and the second motor driver 146a provide power to the first motor 144 and the second motor 146, respectively, in order to cause the first motor 144 and the second motor 146, respectively, to operate. The first motor driver 144a and the second motor driver 146a may alternatively or additionally provide specific instructions to the first motor 144 and the second motor 146, respectively. In some cases, a Hall effect sensor or sensors may alternatively or additionally be used to provide feedback as to the exact location of the distal tip 116.

A controller 202 may be operably coupled with the first motor driver 144a and the second motor driver 146a, and thus may be operably coupled with the first motor 144 and the second motor 146. While illustrated as being separate, in some embodiments the first motor driver 144a and the second motor driver 146a, or at least the functions of the first motor driver 144a and the second motor driver 146a, may be incorporated into the controller 202. The controller 202 may be operably coupled with control inputs 204. The control inputs 204 may schematically represent any apparatus that allows a user to provide control inputs to the controller 202. In some embodiments, the control inputs 204 may include a joystick, such as the joystick 190. In some embodiments, the control inputs 204 may include one, two, three or more buttons such as the buttons 192.

In some embodiments, as shown, the motorized control unit 200 includes a graphical user interface (GUI) 206. In some embodiments, the GUI 206 may include a screen that may be used to display information. The GUI 206 may include a touch screen display, that can be used not only to display information, but also to solicit and receive information. Accordingly, the GUI 206 may be configured to receive inputs from the user, and thus in some instances be considered as being a part of the control inputs 204.

It will be appreciated that the motorized control unit 200 may include additional components not expressly illustrated. For example, each of the individual components of the motorized control unit 200 may include its own power supply, with power being supplied to each individual component at a voltage and current appropriate for that particular individual component. The controller 202 may include a memory, either as part of the controller 202 itself, or operably coupled with the controller 202, for storing algorithms utilized by the controller 202 in controlling various aspects of operation of the motor control assembly 140.

Figure 8:
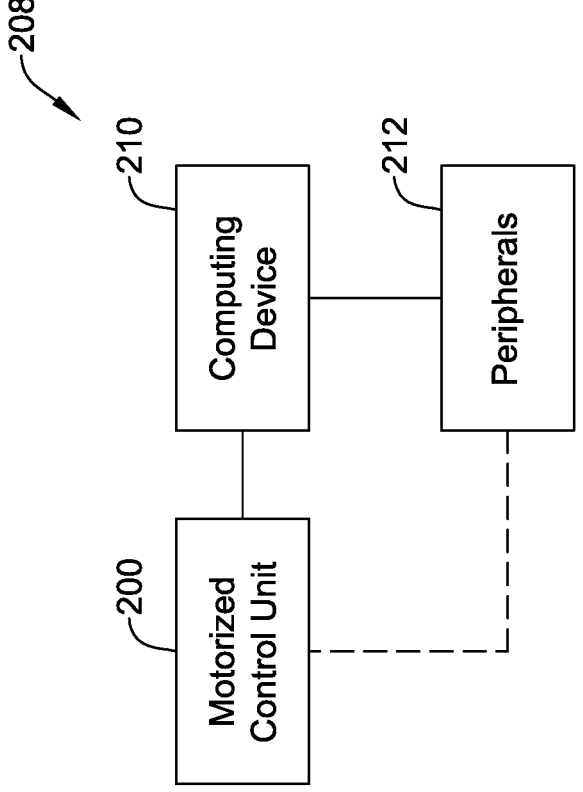
FIG. 8 is a schematic block diagram of an illustrative system including the illustrative motorized control unit of FIG. 7.

FIG. 8 is a schematic block diagram of an illustrative system 208 that includes the motorized control unit 200. As can be seen, in some embodiments the motorized control unit 200 may be operably coupled with a computing device 210. The computing device 210 may represent a desktop computer, a laptop computer, or a workstation. In some embodiments, the computing device 210 may represent a mobile device such as a tablet, a phablet, or even a smart phone. In some embodiments, the computing device 210 may represent a computer server such as a cloud-based server that may be remote from the motorized control unit 200. The computing device 210 may include information entry devices such as but not limited to a keyboard, a mouse, a trackball, a touch pad, a touch screen, and the like, and thus may be considered as providing an additional route (beyond the control inputs 204 shown in FIG. 7) for providing commands to the motorized control unit 200. The computing device 210 may be utilized for monitoring purposes. In some embodiments, the computing device 210 may provide additional functionality to the motor control assembly 140 and hence to the endoscope system 100.

In some embodiments, the system 208 includes peripherals 212 that are operably coupled to the computing device 110. The peripherals 212 may include any peripheral that is advantageously used in combination with the endoscope system 100. As an example, the peripherals 212 may include a camera that is attached to the endoscope 110 that is part of the endoscope system 100. In some embodiments, the camera may include a light source such as an LED or fiber optics. The camera may be used to capture images endoscopically, which may for example be displayed on a display that is provided as part of the computing device 110. Other peripherals are also contemplated. In some embodiments, the peripherals 212 are operably coupled to the computing device 210, and may be controlled by the computing device 210. In some embodiments, at least some peripherals may include their own controller, for example. In some embodiments, the peripherals 212 may alternatively or additionally be coupled directly to the motorized control unit 200.

In some embodiments, a physician operating an endoscope such as the endoscope 110 may desire to improve accuracy in moving the distal tip (such as the distal tip 116 of the endoscope 110) by locking out or preventing movement along one plane while permitting movement along another plane. This may be useful when performing tasks such as but not limited to cannulation, tissue sampling, specimen extraction, and others. With respect to FIG. 7, the controller 202 may be configured to enable a physician or other user to selectively choose between any of multiple modes by providing an appropriate input via the control inputs 204. This may include using a button such as one of the buttons 192, for example. FIG. 9A illustrates a first mode, FIG. 9B illustrates a second mode and FIG. 9C illustrates a third mode.

In the first mode, as shown in FIG. 9A, the distal tip 116 of the endoscope 110 is able to freely move within a first plane 214 and to freely move within a second plane 216. In some instances, the first plane 214 may be considered a left-right plane and the second plane 216 may be considered an up-down plane. In some instances, the first plane 214 may be perpendicular to the second plane 216. In this example, the first plane 214 includes movement of the distal tip 116 to the left and to the right, along an arc 214a that falls within the first plane 214 and the second plane 216 includes movement of the distal tip up and down, along an arc 216a that falls within the second plane 216. When in the first mode, the physician is able to control the motion of the distal tip 116 in both directions (i.e., in the up-down plane and in the left-right plane). In the second mode, as shown in FIG. 9B, the distal tip 116 of the endoscope 110 is able to freely move within the first plane 214 but is constrained from moving within the second plane 216. In this example, the first plane 214 includes movement of the distal tip 116 to the left and to the right, along the arc 214a that falls within the first plane 214 while there is no movement along the arc 216a that falls within the second plane 216. In the third mode, as shown in FIG. 9C, the distal tip 116 of the endoscope 110 is constrained from moving within the first plane 214, along the arc 214a but is able to freely move along the arc 216a that falls within the second plane 216. In the second and third modes, the physician is able to move the distal tip 116 of the endoscope 110 in a single direction while being prevented from moving the distal tip 116 of the endoscope 110 in a second direction. In other words, in the second mode, the controller 202 locks out movement of the distal tip in the second plane 216 (e.g., up-down directions), thus only allowing movement of the distal tip in the first plane 214 (e.g., right-left directions), regardless if the joystick 190 is actuated in the up and/or down directions. In the third mode, the controller 202 locks out movement of the distal tip in the first plane 214 (e.g., right-left directions), thus only allowing movement of the distal tip in the second plane 216 (e.g., up-down directions), regardless if the joystick 190 is actuated in the right and/or left directions. Locked axes will maintain their last commanded position.

In some embodiments, the controller 202 is configured to be able to track a trajectory that is entered by the physician or other user. In some embodiments, the physician or other user may utilize the GUI 206 to enter a trajectory that they want the motor control assembly 140 to follow when controlling movement of the distal tip 116 of the endoscope 100. FIGS. 10A through 10D show example screens that may be displayed on the GUI 206 when the physician or other user wants to enter a trajectory using an input device such as but not limited to the joystick 190. The trajectory may be entered using the computing device 210, or a touch screen, for example. In some embodiments, the desired trajectory may be defined as a collection of waypoints, a starting location and an ending location, or even a traced path. The trajectory may be constrained by the configuration space of the distal tip 116, and the initial and final positions indicated by the trajectory have to exist within the configuration space. If not already there, the physician or other user can use their free hand (the hand not being used to manipulate the joystick 190) to translate the distal tip 116.

Figures 10A, 10B:
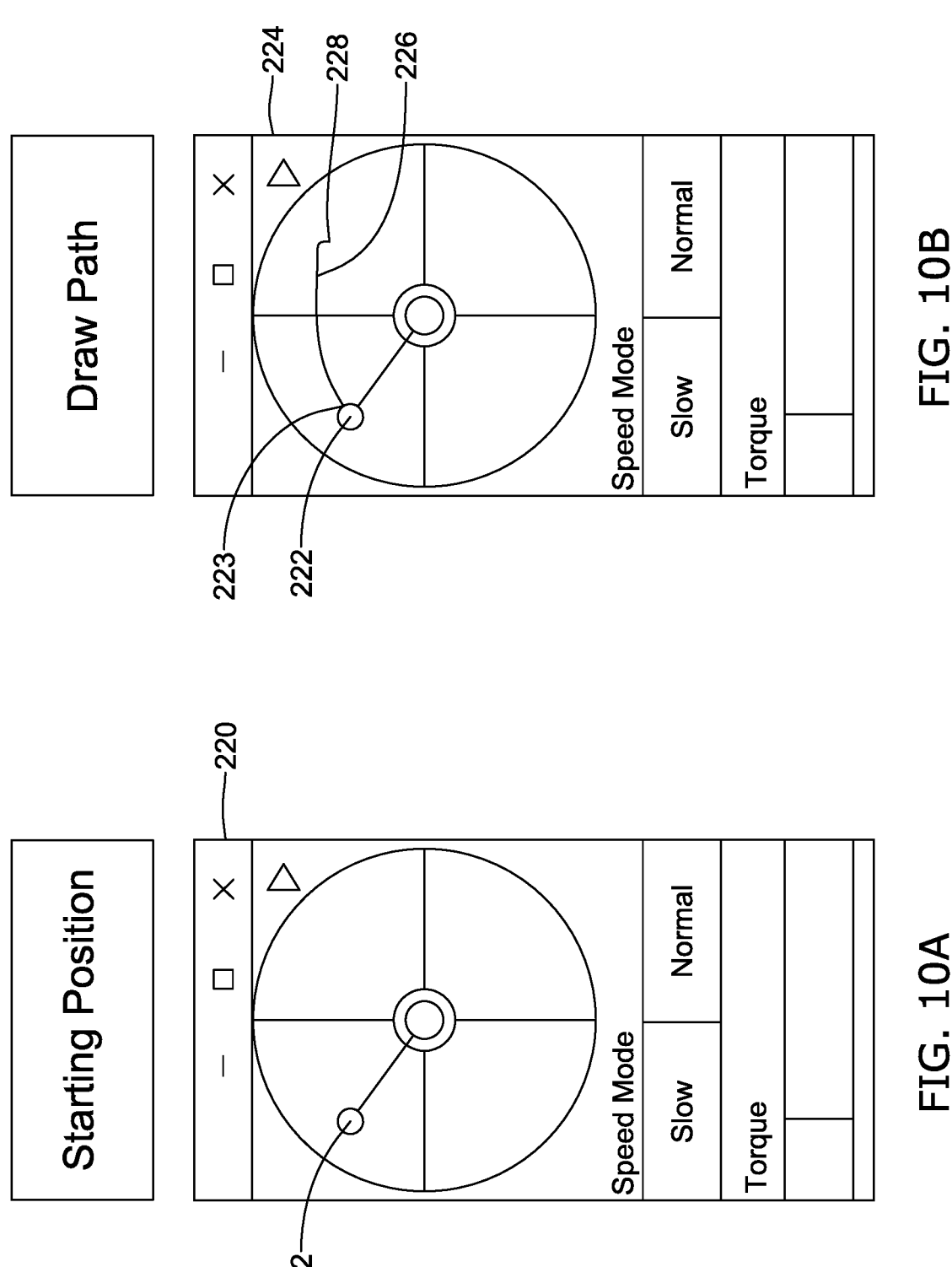
FIGS. 10A, 10B, 10C and 10D show illustrative screens that may be displayed on a graphical user interface (GUI) when a user enters a user-defined trajectory.

FIG. 10A shows a screen 220 that may be considered as representing a starting position. The screen includes a graphical element 222 that indicates a current position of the distal tip 116. In some embodiments, the screen 220 includes an indication of the current speed mode, and may for example display a current torque value. For example, in some cases, the distal tip position with respect to the scope may be provided in a first region of the window on the screen 220, the distal tip speed provided in a second region of the window on the screen 220, and the indication of the amount of force/torque exerted on the distal tip in a third region of the window on the screen 220. In other embodiments, the information may be displayed in more than one window. For example, while not explicitly shown, the distal tip position, distal tip speed, and distal tip force/torque may each be displayed in a separate window. It is further contemplated that the endoscope's camera feed may be displayed in an additional window on the screen 220, or on a separate screen. The physician or other user can enter a trajectory tracking mode by selecting a button such as one of the buttons 192, or through some other data entry mechanism. This causes display of a screen 224, as shown in FIG. 10B. As seen in FIG. 10B, a trajectory 226, with a starting point 223, which is aligned with the graphical element 222 indicating the current position of the distal tip 116 and an end point 228, may be drawn using the joystick, a stylus, the user's finger, or other data entry mechanism. In some embodiments, if the physician or other user is dissatisfied with the trajectory 226 they have drawn, they may have the option of deleting the trajectory 226 and redrawing it.

Figure 10D:
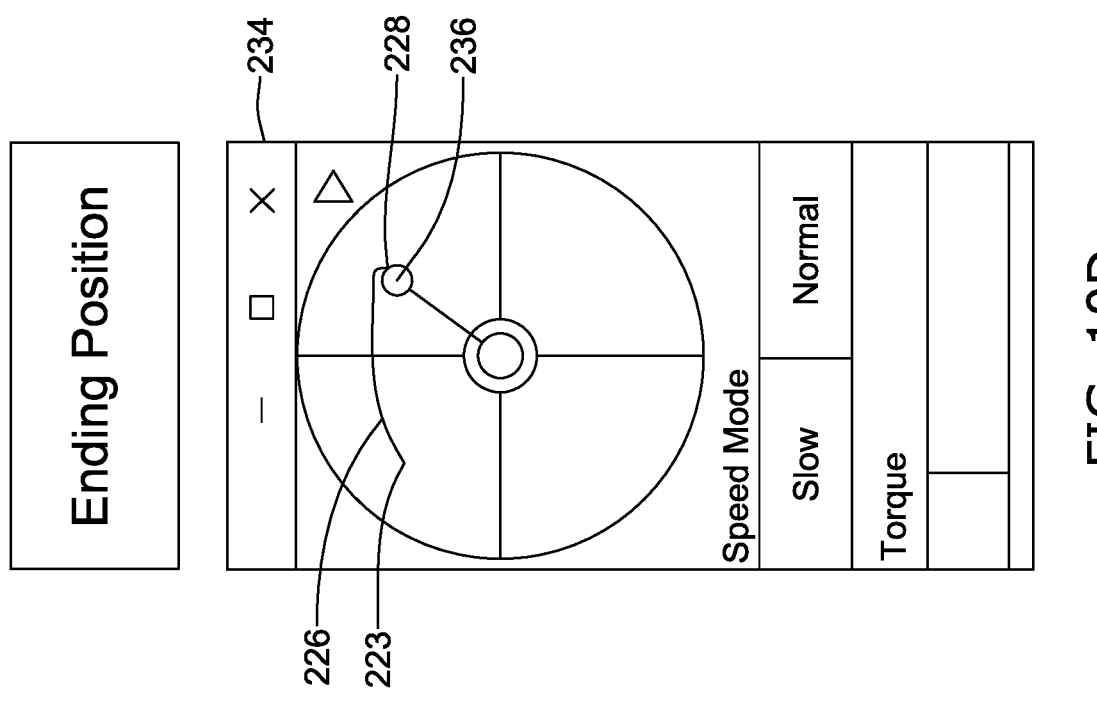
Figure 10C:
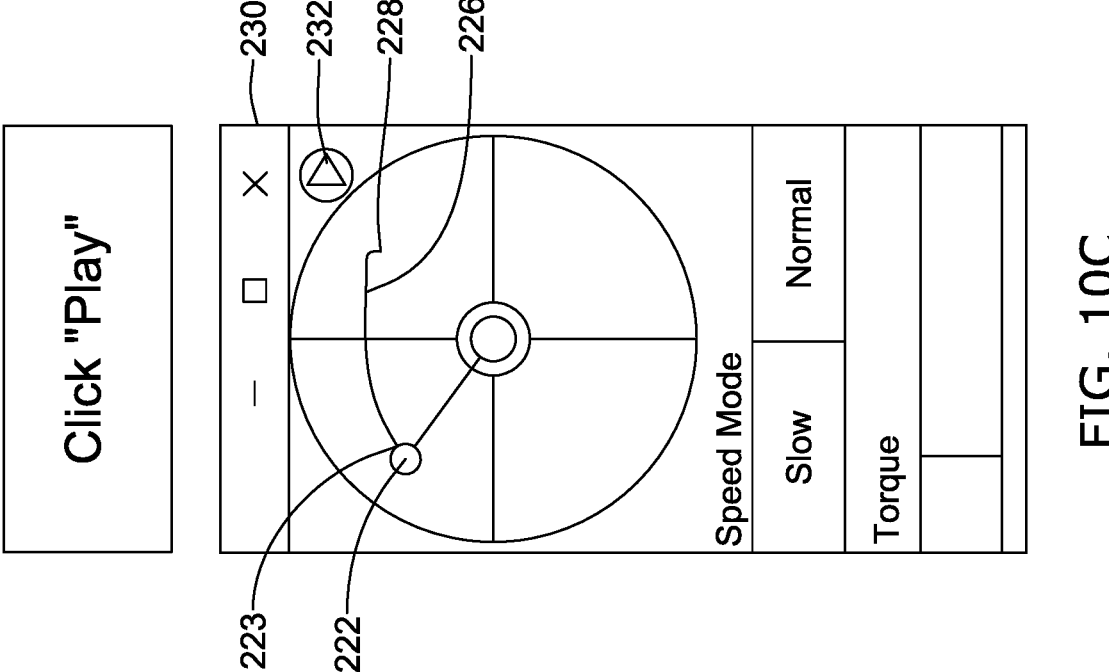

FIG. 10C shows a screen 230 that includes a play button 232. The physician or other user can cause the motor control assembly 140, including the motorized control unit 200, to proceed with moving the distal tip 116 in accordance with the trajectory 226. Once completed, a screen 234, as shown in FIG. 10D, may be displayed indicating that the operation has been completed. It will be appreciated that the graphical element 222, which originally indicated the starting point of the trajectory 226, has now become a graphical element 236 that indicates an ending point of the trajectory 226 and is aligned with the ending point 228 of the trajectory 226.

In some embodiments, the trajectory 226 may be considered as including a number of trajectory waypoints. Each of the trajectory waypoints may be considered as representing a short piece or segment of the trajectory 226. Thus, the trajectory 226 may be approximated with a series of sequential segments, such as linear segments in some instances. In some embodiments, each of the trajectory waypoints may be a short linear approximation of the trajectory 226 as this may simplify the process of following the trajectory 226. In some embodiments, the controller 202 may convert each of the trajectory waypoints into distal tip pose, which gives translational and rotational positions of the distal tip within a Cartesian coordinate system to the controller 202.

In some embodiments, a regression-based technique may be used to estimate the encoder value for each motor that results in the desired pose of the distal tip 116. In some cases, a regression-based technique known as Locally Weighted Projected Regression (LWPR) may be used, although other techniques are contemplated. In some embodiments, an algorithm executed by the controller 202 can approximate a non-linear function in high dimension spaces. At its core, the algorithm uses locally linear models to estimate non-linearity. A learning-based approach may be used to learn a function that maps the pose of the distal tip 116 to motor encoder values. The learned model may be used to calculate the corresponding encoder values based on the desired position of the distal tip 116 of the endoscope 110 and to feed those encoder values to the controller 202 and ultimately to the first motor driver 144a and the second motor driver 146a. In some embodiments, the controller 202 calculates an error between the current encoder values and the desired encoder values and sends appropriate commands to the first motor driver 144a and the second motor driver 146a, as appropriate, to drive the first motor 144 and the second motor 146 appropriately in order to minimize the error between the current encoder values and the desired encoder values. The process may continue until the current encoder values for each of the motors 144, 146 are within a defined threshold from the desired encoder values. In some embodiments, the defined threshold may be predefined. In some cases, the defined threshold may be user-defined.

Figure 11:
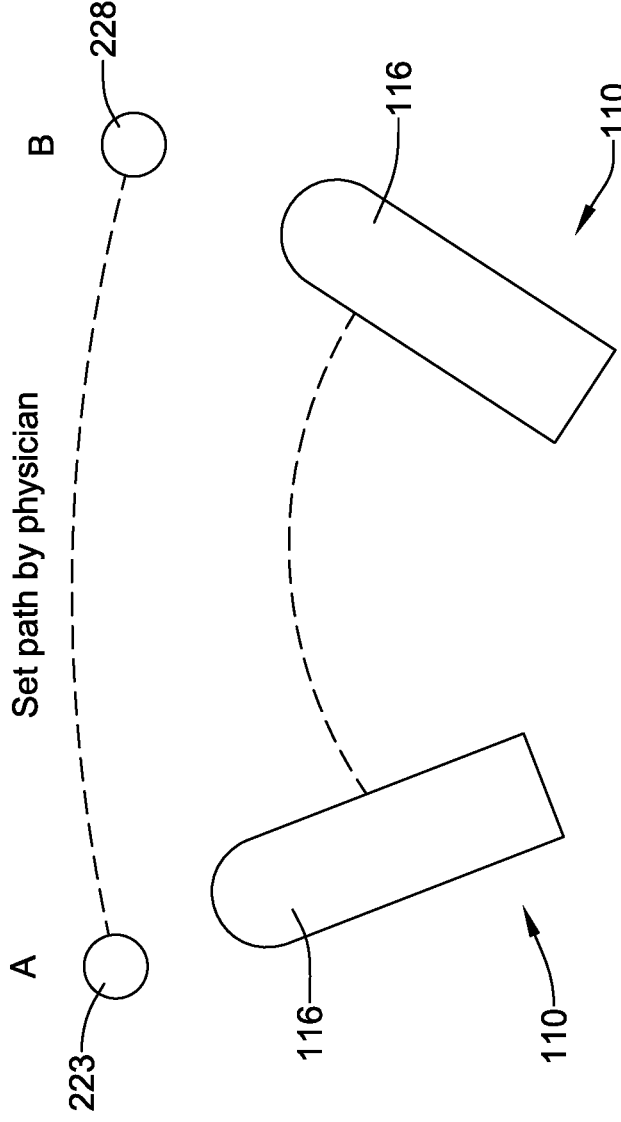
FIG. 11 schematically compares movement of a distal tip of the illustrative endoscope system of FIG. 1 with a corresponding trajectory.

FIG. 11 provides a schematic example of how the distal tip 116 of the endoscope 110 may actually move while following the trajectory 226. In some embodiments, the starting point 223 of the trajectory 226 shows where the distal tip 116 is pointing at the beginning of the trajectory. The ending point 228 of the trajectory 226 may show where the distal tip 116 should be pointing at the end of the trajectory. It will be appreciated that the relative orientation of the distal tip 116 of the endoscope 110 may not be identified by the shape of the trajectory 226. As shown, for example, the relative orientation of the distal tip 116 changes more between the starting point 223 and the ending point 228 than the trajectory 226 would indicate. The trajectory 226 is intended to indicate a change between the starting point 223 and the ending point 228 more so than indicating the relative orientation of the distal tip 116.

Figure 12:
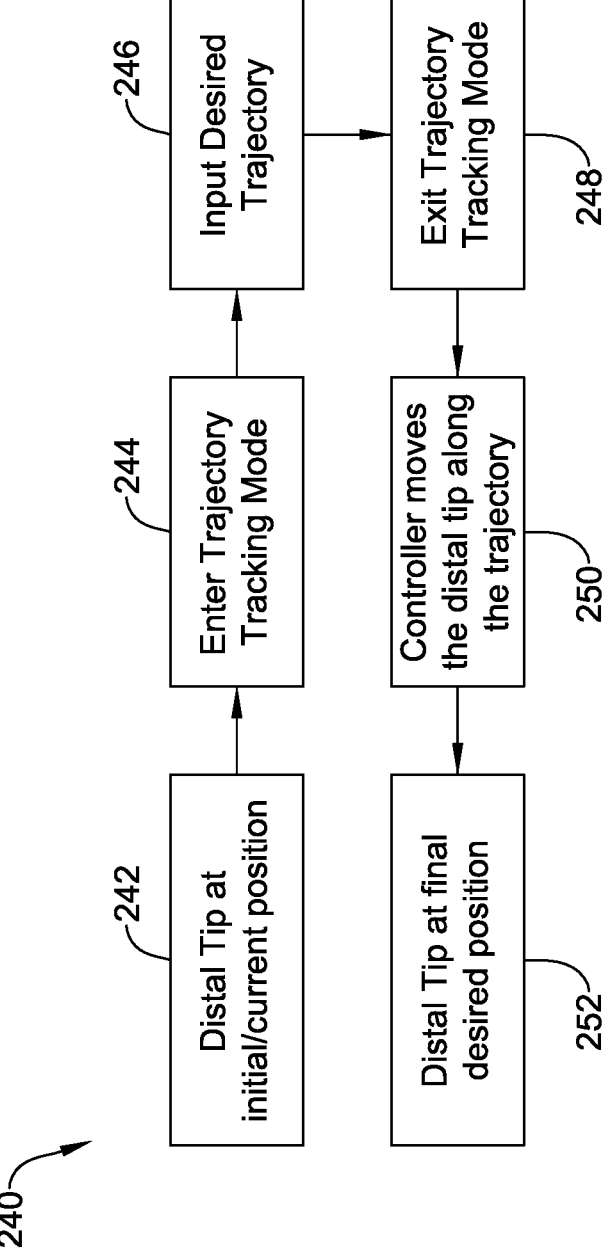
FIG. 12 is a flow diagram showing an illustrative method.

FIG. 12 is a flow diagram showing an illustrative method 240 of following a trajectory such as the trajectory 226. The method 240 may be considered as an example of how the controller 202 follows a trajectory. The method starts with the distal tip 116 being at an initial or current position, as indicated at block 242. This may be considered as being represented by FIG. 10A, for example. The controller 202 enters a Trajectory Tracking Mode, as indicated at block 244. This may be considered as being represented by FIG. 10B, for example. The desired trajectory is entered by the physician or other user, as indicated at block 246. The controller 202 exits the Trajectory Tracking Mode, as indicated at block 248. The controller 202 moves the distal tip 116 along the trajectory, as indicated at block 250. This may be considered as being represented by FIG. 10C, once the physician or other use has selected the play button 232.

In some embodiments, the controller 202 may be configured to accept a target destination from the physician or other user, and to automatically determine an appropriate trajectory to move the distal tip 116 from its current position to a desired position. As an example, the physician or other user may select a desired anatomical feature as shown in a current frame of a camera feed using an input device such as the control inputs 204 (FIG. 7). In some embodiments, the physician or other user may select a desired anatomical feature using a joystick such as the joystick 190, a stylus, the user's finger, a touch screen or perhaps a computer mouse that is coupled with the computing device 210 (FIG. 8). This causes the distal tip 116 to assume a position that would maintain a centered camera frame of the selected feature. This can be especially beneficial in applications in which a continuous and stable line of sight to a particular anatomy during the procedure is desirable.

In some embodiments, it may be desired for the endoscope 110 to maintain a relative position and distance between its distal tip 116 and a desired anatomical landmark or particular anatomy in order to provide stability at the distal tip 116 to the physician or other use and to facilitate performance of parts of the procedure that need minimal tremor and uninterrupted line of sight to particular anatomy. The controller 202 is configured to move the distal tip 116 in such a way that the desired anatomical feature is always kept at the center of the camera frame. After the physician or other use has selected the desired landmark by placing a virtual marker point at the location, the controller 202 is configured to ask the physician or other user to verify the location. If correct, the physician or other user can verify using any suitable input device, such as by pressing one of the buttons 192, accepting a pop-up message on a touch screen, or even through voice inputs. If the physician or other user does not verify the location, the controller 202 may allow them to reselect the marker point.

After verifying selection of the marker point, the algorithm being executed by the controller 202 may calculate the depth and position of the selected anatomical feature with respect to the camera frame and calculates a desired distal tip position of the endoscope 10 that leads to a centered placement of the selected feature with respect to the camera frame, and calculates a trajectory to move to the desired distal tip position. Thus, the trajectory may be calculated by the controller 202 in a semi-autonomous manner. The trajectory is calculated by the algorithm with the initial starting point of the trajectory being the current position of the distal tip 116 and its final position being the position of the distal tip 116 that results in a centered camera frame with respect to the desired anatomical feature selected by the physician or other use while maintaining a comfortable buffer distance between the desired anatomical feature and the distal tip 116. The calculated trajectory is divided into trajectory waypoints that can be followed by the distal tip. The process of following the controller-determined trajectory is essentially the same as the process for following a user-defined trajectory. One difference, in some instances, is that in following the controller-defined trajectory, the controller 202 may be constantly in the loop and generates new trajectories for the distal tip 116 to always minimize its positional error (difference between current encoder values and desired encoder values) until the physician or other user cancels the process.

In some embodiments, the algorithm being executed by the controller 202 evaluates the position of the calculated desired distal tip location and determines if that location is reachable by the distal tip 116 given the current position of the endoscope 110. This calculation may be based upon a total reachable workspace of the distal tip 116 based on its current location. It will be appreciated that the total reachable workspace is a three-dimensional volume surrounding the current location of the distal tip 116. If the desired point falls within this three-dimensional volume, the controller 202 will proceed with automatically generating a feasible path (the trajectory) from the current location of the distal tip 116 to the desired final location of the distal tip 116. However, if there is no feasible trajectory from the current location of the distal tip to the desired final location of the distal tip 116, the controller 202 is configured to notify the physician or other user that they need to move the endoscope 110 to a location that will provide a feasible trajectory from the current location of the distal tip to the desired final location of the distal tip 116. In some embodiments, the controller 202 may utilize auditory and/or visual cues to direct the physician or other user to relocate the endoscope 110 appropriately.

Figure 13:
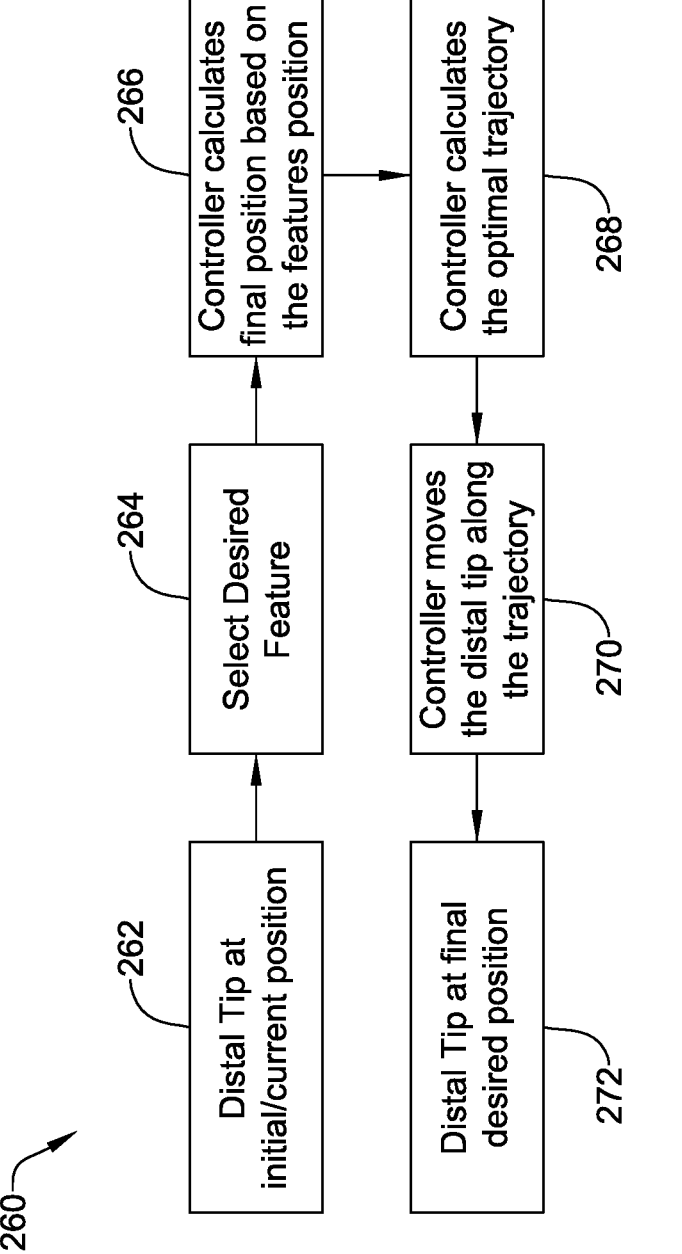
FIG. 13 is a flow diagram showing an illustrative method.

FIG. 13 is a flow diagram showing an illustrative method 260 of determining and following a trajectory in order to reach a desired anatomical feature. The method 260 starts with the distal tip 116 at an initial or current position, as indicated at block 262. The physician or other user is able to select and indicate a desired feature such as a desired anatomical feature, as indicated at block 264. The controller 202 calculates a final position, based on the selected feature, as indicated at block 266. Next, the controller 202 calculates an optimal trajectory, as indicated at block 268. The controller 202 moves the distal tip 116 along the optimal trajectory, as indicated at block 270, by providing appropriate encoder values to the first motor 144 and/or the second motor 146. The method 260 terminates with the distal tip 116 at its final desired position, as indicated at block 272.

Figure 14:
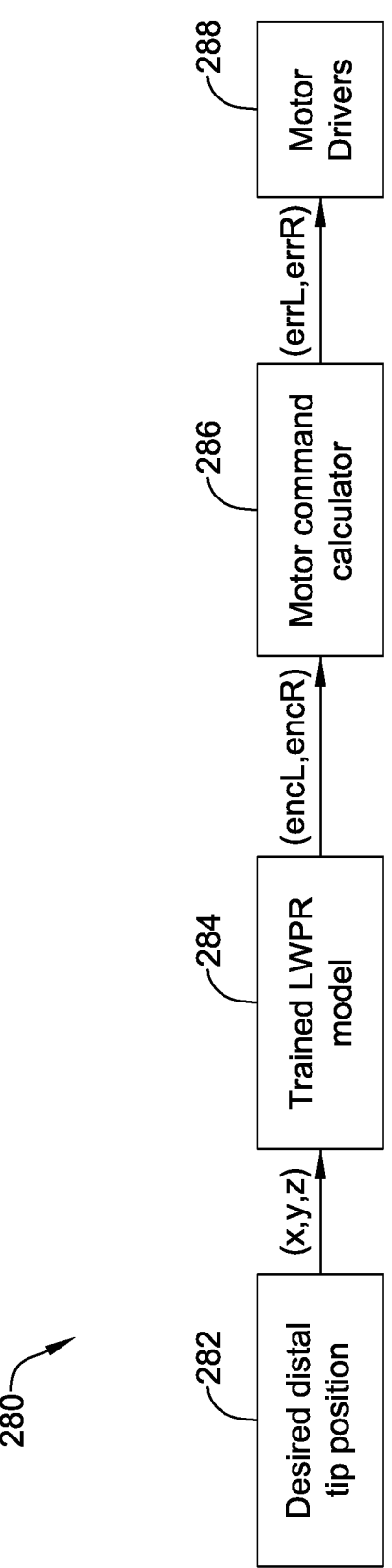
FIG. 14 is a flow diagram showing an illustrative method.

FIG. 14 is a flow diagram showing an illustrative method 280 of how data flows through the algorithm referenced in FIG. 13. The desired distal tip position, as indicated at block 282, is given in Cartesian coordinates (x,y,z). A trained LWPR model receives the (x,y,z) Cartesian coordinates and converts the Cartesian coordinates into encoder step counts (encL and encR), where encL and encR represent the encoder step count for a left encoder and a right encoder (where left and right are arbitrary and merely chosen to separately reference encoders assigned to each of the first motor 144 and the second motor 146). These values are provided to a motor command calculator, as indicated at block 186, which determines errL and errR values, which represent the differences (error) between current encoder counts and desired encoder counts for each of the first motor 144 and the second motor 146. The determined errL and errR values are provided to first motor driver 144a and the second motor driver 146a, as indicated at block 288.

Figure 15:
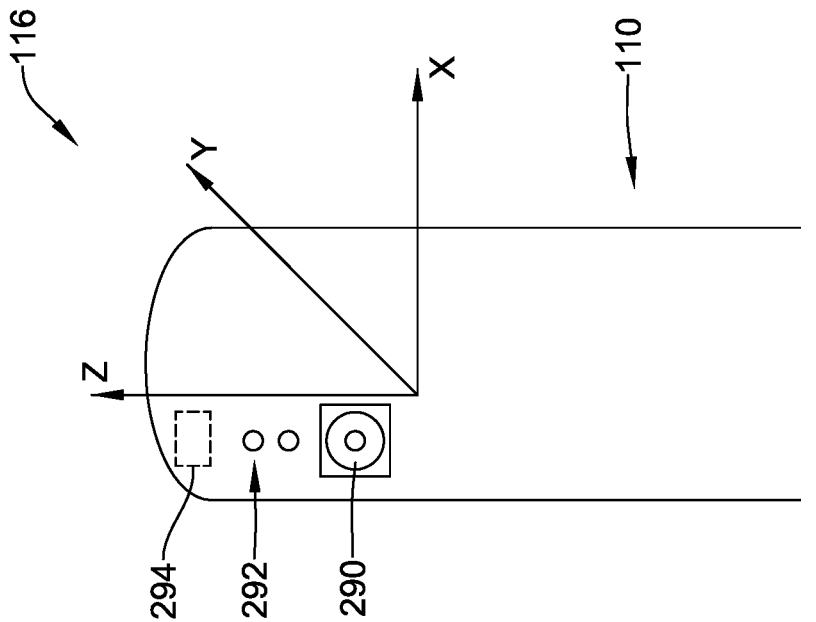
FIG. 15 is a schematic view of a distal region of an illustrative endoscope usable with the illustrative endoscope system of FIG. 1.

FIG. 15 is a schematic view of the distal tip 116 of the endoscope 110. FIG. 15 provides an example of how a Cartesian coordinate system (x,y,z) may be applied to the endoscope 110. FIG. 15 also provides an example of components that may be included as part of the endoscope 110. In some embodiments, the distal tip 116 of the endoscope 110 may include an RGB (red green blue) camera 290. In some embodiments, the distal tip 116 of the endoscope 110 may include a light source 292, such as one or more LEDs. In some embodiments, the distal tip 116 of the endoscope 110 may include a depth sensor 294.

The depth sensor 294 may be used to directly measure a depth (relative to a current location) to a desired anatomical feature. The depth sensor 294 may be a time-of-flight based three-dimensional camera. In some embodiments, the depth may be estimated using various techniques. A monocular camera-based algorithm may be used to estimate depth. Parallel tracking and mapping (PTAM), which uses subsequent video frames to produce a three-dimensional map of point features to approximate the camera pose, and hence, the depth of the camera relative to the selected feature.

In some embodiments, the system, and/or components thereof, may be made from a metal, metal alloy, polymer (some examples of which are disclosed below), a metal-polymer composite, ceramics, combinations thereof, and the like, or other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), MARLEX® high-density polyethylene, MARLEX® low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEV-LAR®), polysulfone, nylon, nylon-12 (such as GRIL-AMID® available from EMS American Grilon), perfluoro (propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, polyure-thane silicone copolymers (for example, ElastEon® from Aortech Biomaterials or ChronoSil® from AdvanSource Biomaterials), biocompatible polymers, other suitable mate-rials, or mixtures, combinations, copolymers thereof, poly-mer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTEL-LOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybde-num alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; platinum; palladium; gold; combinations thereof; or any other suitable material.

In at least some embodiments, portions or all of the system, and/or components thereof, may also be doped with, made of, or otherwise include a radiopaque material. Radiopaque materials are understood to be materials capable of producing a relatively bright image on a fluoroscopy screen or another imaging technique during a medical pro-cedure. This relatively bright image aids the user of the system in determining its location. Some examples of radiopaque materials can include, but are not limited to, gold, platinum, palladium, tantalum, tungsten alloy, polymer material loaded with a radiopaque filler, and the like. Addi-tionally, other radiopaque marker bands and/or coils may also be incorporated into the design of the system to achieve the same result.

In some embodiments, a degree of Magnetic Resonance Imaging (MRI) compatibility is imparted into the system and/or other elements disclosed herein. For example, the system, and/or components or portions thereof, may be made of a material that does not substantially distort the image and create substantial artifacts (i.e., gaps in the image). Certain ferromagnetic materials, for example, may not be suitable because they may create artifacts in an MRI image. The system, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

In some embodiments, the system and/or other elements disclosed herein may include and/or be treated with a suitable therapeutic agent. Some examples of suitable thera-peutic agents may include anti-thrombogenic agents (such as heparin, heparin derivatives, urokinase, and PPack (dextro-phenylalanine proline arginine chloromethylketone)); anti-proliferative agents (such as enoxaparin, angiopeptin, mono-clonal antibodies capable of blocking smooth muscle cell proliferation, hirudin, and acetylsalicylic acid); anti-inflam-matory agents (such as dexamethasone, prednisolone, cor-ticosterone, budesonide, estrogen, sulfasalazine, and mesalamine); antineoplastic/antiproliferative/anti-mitotic agents (such as paclitaxel, 5-fluorouracil, cisplatin, vinblas-tine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD pep-tide-containing compound, heparin, anti-thrombin com-pounds, platelet receptor antagonists, anti-thrombin antibod-ies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcrip-tional activators, and translational promoters); vascular cell growth inhibitors (such as growth factor inhibitors, growth factor receptor antagonists, transcriptional repressors, trans-lational repressors, replication inhibitors, inhibitory antibod-ies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vaso-active mechanisms.

It should be understood that this disclosure is, in many respects, only illustrative. Changes may be made in details, particularly in matters of shape, size, and arrangement of steps without exceeding the scope of the present disclosure. This may include, to the extent that it is appropriate, the use of any of the features of one example embodiment being used in other embodiments. The scope of the present dis-closure is, of course, defined in the language in which the appended claims are expressed.

What is claimed is:

1. A steerable medical device, comprising:
an endoscope including a handle and an elongate shaft extending distally from the handle to a distal tip, wherein the endoscope includes an umbilicus attached to and extending from the handle, the umbilicus con-figured to provide electronic communication between the endoscope and a workstation; and
a motor control assembly including a motor control housing configured to detachably interface with the handle, wherein the umbilicus remains attached to the handle when the motor control housing is detached from the handle;
wherein the motor control assembly includes:
a first drive assembly disposed within the motor control housing;
a second drive assembly disposed within the motor control housing;
an input device; and
a controller operably coupled with the first drive assem-bly, the second drive assembly and the input device, the controller configured to:

control operation of the first drive assembly and/or the second drive assembly in order to move the distal tip;

receive one or more user inputs from a user via the input device; and modify operation of the first drive assembly and/or the second drive assembly in accordance with the received one or more inputs.

2. The steerable medical device of claim 1, wherein:

the first drive assembly comprises a first motor and a first gear assembly operably coupled with the first motor; and the second drive assembly comprises a second motor and a second gear assembly operably coupled with the second motor.

3. The steerable medical device of claim 2, further comprising:

a first drive axle configured to engage the first gear assembly with a first deflection mechanism disposed within the handle, the first deflection mechanism being configured to deflect the distal tip in a first plane; and a second drive axle configured to engage the second gear assembly with a second deflection mechanism disposed within the handle, the second deflection mechanism being configured to deflect the distal tip in a second plane different from the first plane.

4. The steerable medical device of claim 3, wherein the one or more user inputs include a command to lock out movement in either the first plane or the second plane such that:

when the command locks out movement in the first plane, the controller is configured to prevent the first drive assembly from moving the first deflection mechanism while the second drive assembly is permitted to move the second deflection mechanism; and when the command locks out movement in the second plane, the controller is configured to prevent the second drive assembly from moving the second deflection mechanism while the first drive assembly is permitted to move the first deflection mechanism.

5. The steerable medical device of claim 1, wherein the one or more user inputs include a command to move the distal tip along a user-defined trajectory.

6. The steerable medical device of claim 5, wherein the user input device is configured to allow the user to input the user-defined trajectory.

7. The steerable medical device of claim 5, wherein the controller is further configured to operate the first drive assembly and/or the second drive assembly in order to move the distal tip along the user-defined trajectory.

8. The steerable medical device of claim 7, wherein the controller is further configured to implement a learning model in which the controller learns how encoder values for each of the first drive assembly and the second drive assembly relate to corresponding movement of the distal tip.

9. The steerable medical device of claim 8, wherein the controller is further configured to, when moving the first drive assembly and/or the second drive assembly, to minimize a difference between a desired encoder value and a current encoder value.

10. The steerable medical device of claim 1, wherein the one or more user inputs include a command to move the distal tip to a user-defined target.

11. The steerable medical device of claim 10, wherein the user input device is configured to allow the user to input the user-defined target.

12. The steerable medical device of claim 10, wherein the controller is further configured to:

determine a trajectory between a current position of the distal tip and a position defined by the user-defined target; and operate the first drive assembly and/or the second drive assembly in order to move the distal tip along the determined trajectory.

13. A steerable medical device, comprising:

an endoscope including a handle and an elongate shaft extending distally from the handle to a distal tip, wherein the endoscope includes an umbilicus attached to and extending from the handle, the umbilicus configured to provide electronic communication between the endoscope and a workstation; and a motor control assembly including a motor control housing configured to detachably couple with the handle, wherein the umbilicus remains attached to the handle when the motor control housing is detached from the handle;

wherein the motor control assembly includes:

a first drive motor disposed within the motor control housing and configured to cause the distal tip to deflect within a first plane;

a second drive motor disposed within the motor control housing and configured to cause the distal tip to deflect within a second plane different from the first plane;

an input device; and a controller operably coupled with the first drive motor, the second drive motor and the input device, the controller configured to:

receive instructions to move the distal tip along a trajectory;

implement a learning model that indicates how encoder values for each of the first motor and the second motor correspond to movement of the distal tip; and control operation of the first drive motor and/or the second drive motor in order to move the distal tip along the trajectory while minimizing a difference between a desired encoder value and a current encoder value.

14. The steerable medical device of claim 13, wherein the trajectory comprises a user-defined trajectory inputted to the controller.

15. The steerable medical device of claim 14, wherein the input device is configured to allow the user to input the user-defined trajectory.

16. The steerable medical device of claim 13, wherein the trajectory comprises a controller-determined trajectory that is based upon a current position of the distal tip and a desired target location of the distal tip.

17. The steerable medical device of claim 16, wherein the controller is further configured to determine whether the target location of the distal tip is reachable by the distal tip, given a current location of the steerable medical device.

18. The steerable medical device of claim 17, wherein the controller is further configured to:

when the target location of the distal tip is reachable given the current location of the steerable medical device, the controller automatically calculates the controller-determined trajectory; and when the target location of the distal tip is not reachable given the current location of the steerable medical device, the controller provides instructions to the user to move the steerable medical device to a new location that will facilitate reaching the target location of the distal tip.

19. The steerable medical device of claim 17, wherein the controller is further configured to estimate a depth of the target location.

\* \* \* \* \*